US006258945B1

(12) United States Patent
Zimmerman et al.

(10) Patent No.: US 6,258,945 B1
(45) Date of Patent: Jul. 10, 2001

(54) HIV-1P-17 PEPTIDE FRAGMENTS, COMPOSITIONS CONTAINING AND METHODS FOR PRODUCING AND USING SAME

(75) Inventors: Daniel H. Zimmerman, Bethesda; Prem S. Sarin, Gaithersburg, both of MD (US)

(73) Assignee: Viral Technologies INC, Vienna, VA (US)

(*) Notice: Subject to any disclaimer, the term of this patent is extended or adjusted under 35 U.S.C. 154(b) by 0 days.

(21) Appl. No.: 09/588,751

(22) Filed: Jun. 7, 2000

Related U.S. Application Data

(60) Division of application No. 08/824,800, filed on Mar. 26, 1997, now Pat. No. 6,111,068, which is a continuation-in-part of application No. 08/695,301, filed on Aug. 9, 1996, now Pat. No. 6,093,400.

(51) Int. Cl.[7] .................... C07H 21/02
(52) U.S. Cl. .................... 536/23.72; 536/23.1
(58) Field of Search .................... 536/23.1, 23.72

(56) References Cited

U.S. PATENT DOCUMENTS

| | | |
|---|---|---|
| 4,983,387 | 1/1991 | Goldstein et al. . |
| 5,556,744 | 9/1996 | Wiener et al. . |
| 5,580,859 | 12/1996 | Felgner et al. . |
| 5,593,972 | 1/1997 | Weiner et al. . |

FOREIGN PATENT DOCUMENTS

| | | |
|---|---|---|
| 0227169 | 7/1987 | (EP) . |
| 0246829 | 11/1987 | (EP) . |
| 0330359 | 8/1989 | (EP) . |
| 2273709 | 6/1994 | (GB) . |
| 2273710 | 6/1994 | (GB) . |
| 8912548 | 6/1989 | (WO) . |

OTHER PUBLICATIONS

Sarin, et al. Science 232:1135 (1986).
Naylor, et al. Proc. Nat. Acad. Sci. 84:2951 (1981).
Brander, et al. Clin. Exp. Immunol. 101:107 (1995).
Dibrino, et al. J. Immunol. 154(2):620 (1994).
Gazzard, et al. Vaccine Res. 1:129 (1992).
Sarin, et al. Vaccine Res. 3:495 (1994).
Kahn, et al. AIDS Res. Hu. Retroviruses 8:1321 (1992).
Naylor, et al. Int. J. Immunopharm 13(Suppl):117 (1991).
Sarin, et al. Cell. Molec. Biol. 41:401 (1995).
Kahn, et al. Abstract 13 International AIDS Conf.—Jul. 1996.
Talmadge, et al. Clin. Immunol. Meeting, New Orleans—Jun. 1996.
Jiang, et al. J. AIDS 5:382 (1992).
Naylor, et al. Nature 326:549 (1987).
Wahren, et al. J. AIDS 4:448 (1989).
Broliden, et al. Clin. Exp. Immunol. 76:216 (1989).
Papsidero, et al. J. Virol. 63:267 (1989).
Boucher, et al. Clin. Lab. Anal. 4:43 (1990).
Zimmerman, et al. Vaccine Res. 5:91 (1996a).
Zimmerman, et al. Vaccine Res. 5:103 (1996b).
Palker, et al. Proc. Nat. Acad. Sci. 85:1932 (1988).
Clerici, et al. Immuno. Today 14:107 (1993).
Johnson, et al. J. Exp. Med. 176:961 (1992).
Berzofsky, J. Acquire Immun. Deficiency Syndroms 4:451 (1991).
Roitt, I. Essential Immunology, Sixth Eddition, Blackwell Scientific Publications, Boston, MA pp. 173–178.
Kleid, et al. Annals NY Acad. Sci. 413:23–30.
Broekhuijsen, et al. H,/gen. Virol. 68:3137–3143.
Kuwano, et al. J. Exp. Med. 169:1361–1371.
Harrer, et al., HIV–Specific CTL–Response in Healthy Long–Term . . . , IXth Intl. Conf. on AIDS, Berlin, Jun. 1993, Abstract No. POA22–0484, p. 215.
Coates, et al., AIDS Vaccine Predictions. Nature. Apr. 9, 1987, vol. 326, pp. 549–550.
Geysen, et al., Cognitive Features of Continuous Antigenic Determinants, J. Mol. Recog. 1988, vol. 1, No. 1, pp. 32–41.
"The Human Retroviruses and AIDS 1995 . . . " Ed. G. Myers, et al., Theoretical Biology and Biophysics Group, Los Alamos, N.M., pp. I–A–18 to I–A–37.

*Primary Examiner*—Jeffrey Stucker

(57) ABSTRACT

Peptide fragments of the p17 gag protein of HIV-1 from Clade C of from about 30 to about 50 amino acids, including the region extending from position 75 to position 129, raise antibodies recognizing other subtypes, including Clade A, Clade B, Clade E as well as peptides of non-coextensive but overlapping portions of the p17 gag protein. DNA sequences can be used to encode for the peptides of interest. An example of the Clade C peptide of this invention is a peptide having about 30 to about 32 amino acids taken consecutively from a part or the entirety of the following sequence:

```
                                        (SEQ ID NO:2)
                            5                   10
Ala Thr Leu Xaa Xaa Val His Xaa Xaa Ile Xaa Xaa

    15                  20                  20
Xaa Asp Thr Lys Glu Ala Leu Asp Xaa Xaa Xaa Glu

    25                  30                  35
Glu Gln Asn Lys Xaa Gln Gln Lys Xaa Xaa Thr
```

wherein Xaa at position 4 is Tyr or Trp; Xaa at position 5 is Cys or Ser; Xaa at position 8 is Lys, Glu, or Ala; Xaa at position 9 is Gly, Lys, Asp, Glu, or Arg; Xaa at position 11 is Glu; Xaa at position 12 is Val; Xaa at position 13 is Arg; Xaa at position 21 is Lys; Xaa at position 22 is Ile; Xaa at position 23 is Glu or Lys; Xaa at position 29 is Ile, Ser or Cys; Xaa at position 33 is a direct bond; and Xaa at position 34 is a direct bond.

1 Claim, 3 Drawing Sheets

SEQUENCE LISTING (1) GENERAL INFORMATION:

(iii) NUMBER OF SEQUENCES:24

(2) INFORMATION FOR SEQ ID NO: 1:

(i) SEQUENCE CHARACTERISTICS:
(A) LENGTH:55 amino acids
(B) TYPE:amino acid
(C) TOPOLOGY:linear (ii) MOLECULE TYPE:peptide (v) FRAGMENT TYPE:internal fragment (vi) ORIGINAL SOURCE:
(A) ORGANISM:HIV-1

(ix) FEATURE:
(A) NAME/KEY:Consensus C of p17 protein
(B) LOCATION:1-55
(C) IDENTIFICATION METHOD:etablished consensus sequence
(D) OTHER INFORMATION:residues 75 to 129

(xi) SEQUENCE DESCRIPTION:SEQ ID NO:1:

```
Xaa Ser Leu Xaa Asn Thr Val Xaa Xaa Leu Xaa Xaa Val His Xaa Xaa
                5                   10                  15

Ile Xaa Xaa Xaa Asp Thr Lys Glu Ala Leu Asp Xaa Xaa Xaa Glu Glu
            20                  25                  30

Gln Asn Lys Xaa Gln Gln Lys Xaa Xaa Thr Xaa Xaa Xaa Xaa Xaa Ala
        35                  40                  45

Asp Xaa Gly Xaa Val Ser Gln
    50                  55
```

(2) INFORMATION FOR SEQ ID NO: 2:

(i) SEQUENCE CHARACTERISTICS:
(A) LENGTH:35 amino acids
(B) TYPE:amino acid
(C) TOPOLOGY:linear (ii) MOLECULE TYPE:peptide (v) FRAGMENT TYPE:internal fragment (vi) ORIGINAL SOURCE:
(A) ORGANISM:HIV-1

(ix) FEATURE:
(A) NAME/KEY:Consensus C of p17 protein
(B) LOCATION:1-35
(C) IDENTIFICATION METHOD:established consensus sequence
(D) OTHER INFORMATION:residues 82-116

(xi) SEQUENCE DESCRIPTION:SEQ ID NO:2:

```
Ala Thr Leu Xaa Xaa Val His Xaa Xaa Ile Xaa Xaa Xaa Asp Thr Lys
                5                   10                  15

Glu Ala Leu Asp Xaa Xaa Xaa Glu Glu Gln Asn Lys Xaa Gln Gln Lys
            20                  25                  30

Xaa Xaa Thr
        35
```

(2) INFORMATION FOR SEQ ID NO: 3:

(i) SEQUENCE CHARACTERISTICS:
(A) LENGTH:30 amino acids

-continued (B) TYPE:amino acid
(C) TOPOLOGY:linear (ii) MOLECULE TYPE:peptide (v) FRAGMENT TYPE:internal fragment (vi) ORIGINAL SOURCE:
(A) ORGANISM:HIV-1
(B) STRAIN:HIV SF2

(ix) FEATURE:
(A) NAME/KEY:HGP-30
(B) LOCATION:1-3
(C) IDENTIFICATION METHOD:established consensus sequence
(D) OTHER INFORMATION:Consensus A sequence, residues of p17 gag protein at positions 86-115

(xi) SEQUENCE DESCRIPTION:SEQ ID NO: 3:

```
Tyr Ser Val His Gln Arg Ile Asp Val Lys Asp Thr Lys Glu Ala Leu
                5                   10                  15

Glu Lys Ile Glu Glu Glu Gln Asn Lys Ser Lys Lys Lys Ala
            20                  25                  30
```

(2) INFORMATION FOR SEQ ID NO: 4:

(i) SEQUENCE CHARACTERISTICS:
(A) LENGTH:30 amino acids
(B) TYPE:amino acid
(C) TOPOLOGY:linear (ii) MOLECULE TYPE:peptide (v) FRAGMENT TYPE:internal fragment (vi) ORIGINAL SOURCE:
(A) ORGANISM:HIV-1

(ix) FEATURE:
(A) NAME/KEY:Thailand B Consensus sequence
(B) LOCATION:1-30
(C) IDENTIFICATION METHOD: established consensus sequence
(D) OTHER INFORMATION:Consensus C sequence, residues of p17 gag protein at positions 86-115

(xi) SEQUENCE DESCRIPTION:SEQ ID NO: 4:

```
Tyr Cys Val His Gln Lys Ile Glu Val Lys Asp Thr Lys Glu Ala Leu
                5                   10                  15

Glu Lys Ile Glu Glu Glu Gln Asn Lys Ser Lys Lys Lys Ala
            20                  25                  30
```

(2) INFORMATION FOR SEQ ID NO: 5:

(i) SEQUENCE CHARACTERISTICS:
(A) LENGTH:30 amino acids
(B) TYPE:amino acid
(C) TOPOLOGY:linear (ii) MOLECULE TYPE:peptide (v) FRAGMENT TYPE:internal fragment (vi) ORIGINAL SOURCE:
(A) ORGANISM:HIV-1

(ix) FEATURE:
(A) NAME/KEY:Uganda C Consensus sequence
(B) LOCATION:1-30
(C) IDENTIFICATION METHOD:established consensus sequence
(D) OTHER INFORMATION:Consensus C sequence, residues of p17 gag protein at positions 86-115

(xi) SEQUENCE DESCRIPTION:SEQ ID NO: 5:

-continued

Tyr Cys Val His Lys Gly Ile Glu Val Arg Asp Thr Lys Glu Ala Leu
5 10 15

Asp Lys Ile Glu Glu Glu Gln Asn Lys Ile Gln Gln Lys Thr
20 25 30

(2) INFORMATION FOR SEQ ID NO: 6:

(i) SEQUENCE CHARACTERISTICS:
(A) LENGTH:30 amino acids
(B) TYPE:amino acids
(C) STRANDEDNESS:
(D) TOPOLOGY:linear (ii) MOLECULE TYPE:peptide (v) FRAGMENT TYPE:internal fragment (vi) ORIGINAL SOURCE:
(A) ORGANISM:HIV-1

(ix) FEATURE:
(A) NAME/KEY:Thailand E Consensus sequence
(B) LOCATION:1-30
(C) IDENTIFICATION METHOD:established consensus sequence
(D) OTHER INFORMATION:Consensus E sequence, residues of p17 gag protein at positions 86-115

(xi) SEQUENCE DESCRIPTION:SEQ ID NO: 6:

Trp Cys Val His Gln Arg Ile Glu Val Lys Asp Thr Lys Glu Ala Leu
5 10 15

Asp Lys Ile Glu Glu Val Gln Asn Lys Ser Gln Gln Lys Thr
20 25 30

(2) INFORMATION FOR SEQ ID NO: 7:

(i) SEQUENCE CHARACTERISTICS:
(A) LENGTH:29 amino acids
(B) TYPE:amino acid
(C) TOPOLOGY:linear (ii) MOLECULE TYPE:peptide (v) FRAGMENT TYPE:internal fragment (vi) ORIGINAL SOURCE:
(A) ORGANISM:HIV-1
(B) STRAIN:HIV SF2

(ix) FEATURE:
(A) NAME/KEY:modified HGP-30
(B) LOCATION:1-29
(C) IDENTIFICATION METHOD:established consensus sequence
(D) OTHER INFORMATION:Consensus A sequence, residues of p17 gag protein at positions 83-111

(xi) SEQUENCE DESCRIPTION:SEQ ID NO: 7:

Ala Thr Leu Tyr Ser Val His Gln Arg Ile Asp Val Lys Asp Thr Lys
5 10 15

Glu Ala Leu Glu Lys Ile Glu Glu Glu Gln Asn Lys Ser
20 25

(2) INFORMATION FOR SEQ ID NO: 8:

(i) SEQUENCE CHARACTERISTICS:
(A) LENGTH:55 amino acids
(B) TYPE:amino acid
(C) TOPOLOGY:linear (ii) MOLECULE TYPE:peptide -continued (v) FRAGMENT TYPE:internal fragment (vi) ORIGINAL SOURCE:
(A) ORGANISM:HIV-1

(ix) FEATURE:
(A) NAME/KEY:Consensus C sequence
(B) LOCATION:1-55
(C) IDENTIFICATION METHOD:established consensus sequence
(D) OTHER INFORMATION:residues 75-129 of p17 protein (xi) SEQUENCE DESCRIPTION:SEQ ID NO: 8:

```
Arg Ser Leu Xaa Asn Thr Val Ala Thr Leu Tyr Cys Val His Xaa Xaa
                5                   10                  15

Ile Glu Val Arg Asp Thr Lys Glu Ala Leu Asp Lys Ile Glu Glu Glu
            20                  25                  30

Gln Asn Lys Xaa Gln Gln Lys Xaa Xaa Thr Gln Gln Ala Lys Xaa Ala
        35                  40                  45

Asp Xaa Gly Lys Val Ser Gln
    50                  55
```

(2) INFORMATION FOR SEQ ID NO: 9:

(i) SEQUENCE CHARACTERISTICS:
(A) LENGTH:50 amino acids
(B) TYPE:amino acid
(C) TOPOLOGY:linear (ii) MOLECULE TYPE:peptide (v) FRAGMENT TYPE:internal fragment (vi) ORIGINAL SOURCE:
(A) ORGANISM:HIV-1
(B) STRAIN:HIV UG268

(ix) FEATURE:
(A) NAME/KEY:HIV UG268
(B) LOCATION:1-3
(C) IDENTIFICATION METHOD:established consensus sequence
(D) OTHER INFORMATION:residues 76-125 of p17 protein (xi) SEQUENCE DESCRIPTION:SEQ ID NO: 9:

```
Arg Ser Leu Tyr Asn Thr Val Ala Thr Leu Tyr Cys Val His Lys Gly
                5                   10                  15

Ile Glu Val Arg Asp Thr Lys Glu Ala Leu Asp Lys Ile Glu Glu Glu
            20                  25                  30

Gln Asn Lys Ile Gln Gln Lys Thr Glu Thr Ala Asp Lys Gly Lys Val
        35                  40                  45

Ser Gln
    50
```

(2) INFORMATION FOR SEQ ID NO:10:

(i) SEQUENCE CHARACTERISTICS:
(A) LENGTH:52 amino acids
(B) TYPE:amino acids
(C) TOPOLOGY:linear (ii) MOLECULE TYPE:peptide (v) FRAGMENT TYPE:internal fragment (vi) ORIGINAL SOURCE:
(A) ORGANISM:HIV-1
(B) STRAIN:HIV SM145

(ix) FEATURE:
(A) NAME/KEY:HIV SM145

(B) LOCATION:1-52
(C) IDENTIFICATION METHOD:established consensus sequence
(D) OTHER INFORMATION:residues 76-127 of p17 protein (xi) SEQUENCE DESCRIPTION:SEQ ID NO: 10:

```
Arg Ser Leu Phe Asn Thr Val Ala Thr Leu Tyr Cys Val His Glu Lys
                5                   10                  15

Ile Glu Val Arg Asp Thr Lys Glu Ala Leu Asp Lys Ile Glu Glu Glu
            20                  25                  30

Gln Asn Lys Ser Gln Gln Lys Thr Gln Gln Ala Lys Ala Ala Asp Gly
        35                  40                  45

Lys Val Ser Gln
    50
```

(2) INFORMATION FOR SEQ ID NO:11:

(i) SEQUENCE CHARACTERISTICS:
(A) LENGTH:54 amino acids
(B) TYPE:amino acid
(C) TOPOLOGY:linear (ii) MOLECULE TYPE:peptide (v) FRAGMENT TYPE:internal fragment (vi) ORIGINAL SOURCE:
(A) ORGANISM:HIV-1
(B) STRAIN:HIV ZAM18

(ix) FEATURE:
(A) NAME/KEY:HIV ZAM18
(B) LOCATION:1-54
(C) IDENTIFICATION METHOD:established consensus sequence
(D) OTHER INFORMATION:residues 76-128 of p17 protein (xi) SEQUENCE DESCRIPTION:SEQ ID NO: 11:

```
Lys Ser Leu Phe Asn Thr Val Val Thr Leu Trp Cys Val His Glu Asp
                5                   10                  15

Ile Thr Val Arg Asp Thr Lys Glu Ala Leu Asp Arg Leu Glu Glu Glu
            20                  25                  30

Gln Asn Lys Ser Gln Gln Lys Thr Lys Thr Gln Gln Ala Lys Ala Ala
        35                  40                  45

Asp Gly Lys Val Ser Gln
    50
```

(2) INFORMATION FOR SEQ ID NO: 12:

(i) SEQUENCE CHARACTERISTICS:
(A) LENGTH:52 amino acids
(B) TYPE:amino acid
(C) TOPOLOGY:linear (ii) MOLECULE TYPE:peptide (v) FRAGMENT TYPE:internal fragment (vi) ORIGINAL SOURCE:
(A) ORGANISM:HIV-1
(B) STRAIN:HIV ZAM19

(ix) FEATURE:
(A) NAME/KEY:HIV ZAM19
(B) LOCATION:1-52
(C) IDENTIFICATION METHOD:established consensus sequence
(D) OTHER INFORMATION:residues 76-127 of p17 protein (xi) SEQUENCE DESCRIPTION:SEQ ID NO: 12:

```
Lys Ser Leu His Asn Ala Val Ala Val Leu Tyr Cys Val His Lys Xaa
```

-continued

```
                5                   10                  15

Ile Thr Val Arg Asp Thr Lys Glu Ala Leu Asp Arg Ile Glu Glu Glu
            20                  25                  30

Gln Asn Lys Cys Gln Gln Lys Thr Gln Gln Ala Lys Glu Ala Asp Gly
        35                  40                  45

Lys Val Ser Gln
    50
```

(2) INFORMATION FOR SEQ ID NO: 13:

(i) SEQUENCE CHARACTERISTICS:
(A) LENGTH:52 amino acids
(B) TYPE:amino acid
(C) TOPOLOGY:linear (ii) MOLECULE TYPE:peptide (v) FRAGMENT TYPE:internal fragment (vi) ORIGINAL SOURCE:
(A) ORGANISM:HIV-1
(B) STRAIN:HIV ZAM20

(ix) FEATURE:
(A) NAME/KEY:HIV ZAM20
(B) LOCATION:1052
(C) IDENTIFICATION METHOD:established consensus sequence
(D) OTHER INFORMATION:residues 76-127 of p17 protein (xi) SEQUENCE DESCRIPTION:SEQ ID NO: 13:

```
Arg Ser Leu Tyr Asn Thr Val Ala Thr Leu Tyr Cys Val His Ala Gly
                5                   10                  15

Ile Glu Val Arg Asp Thr Lys Glu Ala Leu Asp Glu Ile Glu Glu Glu
            20                  25                  30

Gln Asn Lys Cys Gln Gln Lys Thr Gln Gln Ala Lys Thr Ala Asp Gly
        35                  40                  45

Lys Val Ser Gln
    50
```

(2) INFORMATION FOR SEQ ID NO: 14:

(i) SEQUENCE CHARACTERISTICS:
(A) LENGTH:53 amino acids
(B) TYPE:amino acid
(C) TOPOLOGY:linear (ii) MOLECULE TYPE:peptide (v) FRAGMENT TYPE:internal fragment (vi) ORIGINAL SOURCE:
(A) ORGANISM:HIV-1
(B) STRAIN:HIV DJ259

(ix) FEATURE:
(A) NAME/KEY:HIV DJ259
(B) LOCATION:1-53
(C) IDENTIFICATION METHOD:established consensus sequence
(D) OTHER INFORMATION:residues 76-128 of p17 protein (xi) SEQUENCE DESCRIPTION:SEQ ID NO: 14:

```
Arg Ser Leu Tyr Asn Thr Val Ala Thr Leu Tyr Cys Val His Ala Arg
                5                   10                  15

Ile Glu Ile Gln Asp Thr Lys Glu Ala Leu Asp Lys Ile Glu Glu Glu
            20                  25                  30

Gln Asn Lys Cys Gln Gln Lys Thr Gln Lys Ala Glu Thr Ala Asp Lys
        35                  40                  45
```

-continued

```
Gly Lys Val Ser Gln
    50


(2) INFORMATION FOR SEQ ID NO: 15:

     (i) SEQUENCE CHARACTERISTICS:
          (A) LENGTH:53 amino acids
          (B) TYPE:amino acid
          (C) TOPOLOGY:linear

    (ii) MOLECULE TYPE:peptide

     (v) FRAGMENT TYPE:internal fragment

    (vi) ORIGINAL SOURCE:
          (A) ORGANISM:HIV-1
          (B) STRAIN:HIV VI313

    (ix) FEATURE:
          (A) NAME/KEY:HIV VI313
          (B) LOCATION:1-53
          (C) IDENTIFICATION METHOD:established consensus sequence
          (D) OTHER INFORMATION:residues 76-128 of p17 protein

    (xi) SEQUENCE DESCRIPTION:SEQ ID NO: 15:

Ile Ser Leu His Asn Thr Val Ala Thr Leu Tyr Cys Val His Glu Lys
                5                   10                  15

Ile Glu Ile Arg Asp Thr Lys Glu Ala Leu Asp Lys Ile Glu Gly Glu
            20                  25                  30

Gln Asn Lys Ser Gln Gln Lys Thr Gln Gln Ala Ala Ala Ala Asp Asn
        35                  40                  45

Gly Lys Val Ser Gln
    50


(2) INFORMATION FOR SEQ ID NO: 16:

     (i) SEQUENCE CHARACTERISTICS:
          (A) LENGTH:165 base pairs
          (B) TYPE:nucleic acid
          (C) STRANDEDNESS:single
          (D) TOPOLOGY:linear

    (ii) MOLECULE TYPE:genomic DNA

    (vi) ORIGINAL SOURCE:
          (A) ORGANISM:HIV-1

  (viii) POSITION IN GENOME:226 to 380 of p17 gag protein

    (ix) FEATURE:
          (A) NAME/KEY:
          (B) LOCATION:1-165
          (C) IDENTIFICATION METHOD:established consensus sequence

    (xi) SEQUENCE DESCRIPTION:SEQ ID NO: 16:

AGA TCA TTA TAT AAC ACA GTA GCA ACT CTC TAT TGT GTA CAT GAA NAG       48
Arg Ser Leu Tyr Asn Thr Val Ala Thr Leu Tyr Cys Val His Glu Xaa
                5                   10                  15

ATA GAG GTA CGA GAC ACC AAG GAA GCC TTA GAC AAG ATA GAG GAA GAA       96
Ile Glu Val Arg Asp Thr Lys Glu Ala Leu Asp Lys Ile Glu Glu Glu
            20                  25                  30

CAA AAC AAA AGT CAG CAA AAA NNN NNN ACA CAG CAG GCA AAA GCG GCT      144
Gln Asn Lys Ser Gln Gln Lys Xaa Xaa Thr Gln Gln Ala Lys Ala Ala
        35                  40                  45

GAC NNN GGA AAG GTC AGT CAA                                          165
Asp Xaa Gly Lys Val Ser Gln
    50                  55
```

-continued

```
(2) INFORMATION FOR SEQ ID NO: 17:

     (i) SEQUENCE CHARACTERISTICS:
          (A) LENGTH:150 base pairs
          (B) TYPE:nucleic acid
          (C) STRANDEDNESS:single
          (D) TOPOLOGY:linear

    (ii) MOLECULE TYPE:genomic DNA

    (vi) ORIGINAL SOURCE:
          (A) ORGANISM:HIV-1
          (B) STRAIN:HIV UG268

  (viii) POSITION IN GENOME:213 to 375 of p17 gag protein

    (ix) FEATURE:
          (A) NAME/KEY:
          (B) LOCATION:1-150
          (C) IDENTIFICATION METHOD:established consensus sequence

    (xi) SEQUENCE DESCRIPTION:SEQ ID NO: 17:

AGA TCA TTA TAT AAC ACA GTA GCA ACT CTC TAT TGT GTA CAT AAA GGG       48
Arg Ser Leu Tyr Asn Thr Val Ala Thr Leu Tyr Cys Val His Lys Gly
                5                  10                  15

ATA GAG ATA CGA GAC ACC AAG GAA GCC TTA GAC AAG ATA GAG GAA GAA       96
Ile Glu Ile Arg Asp Thr Lys Glu Ala Leu Asp Lys Ile Glu Glu Glu
            20                  25                  30

CAA AAC AAG ATT CAG CAA AAA ACA GAA ACA GCT GAC AAA GGA AAG GTC      144
Gln Asn Lys Ser Gln Gln Lys Thr Glu Thr Ala Asp Lys Gly Lys Val
        35                  40                  45

AGT CAA                                                              150
Ser Glu
    50


(2) INFORMATION FOR SEQ ID NO: 18:

     (i) SEQUENCE CHARACTERISTICS:
          (A) LENGTH:156 base pairs
          (B) TYPE:nucleic acid
          (C) STRANDEDNESS:single
          (D) TOPOLOGY:linear

    (ii) MOLECULE TYPE:genomic DNA

    (vi) ORIGINAL SOURCE:
          (A) ORGANISM:HIV SM145

  (viii) POSITION IN GENOME:213 to 381 of p17 gag protein

    (ix) FEATURE:
          (A) NAME/KEY:
          (B) LOCATION:1-156
          (C) IDENTIFICATION METHOD:established consensus sequence

    (xi) SEQUENCE DESCRIPTION:SEQ ID NO: 18:

AGA TCA TTA TTC AAC ACA GTA GCA ACT CTC TAT TGT GTA CAT GAA AAG       48
Arg Ser Leu Phe Asn Thr Val Ala Thr Leu Tyr Cys Val His Glu Lys
                5                  10                  15

ATA GAT GTA CGA GAC ACC AAG GAA GCC TTA GAC AAG ATA GAG GAA GAA       96
Ile Glu Val Arg Asp Thr Lys Glu Ala Leu Asp Lys Ile Glu Glu Glu
            20                  25                  30

CAA AAC AAA AGT CAG CAA AAA ACA CAG CAG GCA AAA GCG GCT GAC GGA      144
Gln Asn Lys Ser Gln Gln Lys Thr Gln Gln Ala Lys Ala Ala Asp Gly
        35                  40                  45

AAG GTC AGT CAA                                                      156
Lys Val Ser Gln
    50
```

-continued (2) INFORMATION FOR SEQ ID NO: 19:

(i) SEQUENCE CHARACTERISTICS:
(A) LENGTH:162 base pairs
(B) TYPE:nucleic acid
(C) STRANDEDNESS:single
(C) TOPOLOGY:linear (ii) MOLECULE TYPE:genomic DNA (vi) ORIGINAL SOURCE:
(A) ORGANISM:HIV ZAM18

(viii) POSITION IN GENOME:213 to 387 of p17 gag protein (ix) FEATURE:
(A) NAME/KEY:
(B) LOCATION:1-162
(C) IDENTIFICATION METHOD:established consensus sequence (xi) SEQUENCE DESCRIPTION:SEQ ID NO: 19:

```
AAA TCA TTA TTC AAC ACA GTA GTA ACT CTA TGG TGT GTA CAT GAA GAT       48
Lys Ser Leu Phe Asn Thr Val Val Thr Leu Trp Cys Val His Glu Asp
                5                  10                  15

ATA ACA GTA CGA GAC ACC AAG GAA GCC TTA GAC AGA TTA GAC GAA GAA       96
Ile Thr Val Arg Asp Thr Lys Glu Ala Leu Asp Arg Leu Glu Glu Glu
            20                  25                  30

CAA AAC AAA AGT CAG CAA AAA ACA AAA ACA CAG CAG GCA AAA GCG GCT      144
Gln Asn Lys Ser Gln Gln Lys Thr Lys Thr Gln Gln Ala Lys Ala Ala
        35                  40                  45

GAC GGA CAG GTC AGT CAA                                              162
Asp Cly Gln Val Ser Gln
    50
```

(2) INFORMATION FOR SEQ ID NO: 20:

(i) SEQUENCE CHARACTERISTICS:
(A) LENGTH:156 base pairs
(B) TYPE:nucleic acid
(C) STRANDEDNESS:single
(D) TOPOLOGY:linear (ii) MOLECULE TYPE:genomic DNA (vi) ORIGINAL SOURCE:
(A) ORGANISM:HIV ZAM19

(viii) POSITION IN GENOME:213 to 381 of p17 gag protein (ix) FEATURE:
(A) NAME/KEY:
(B) LOCATION:1-156
(C) IDENTIFICATION METHOD:established consensus sequence (xi) SEQUENCE DESCRIPTION:SEQ ID NO: 20:

```
AAA TCA TTA CAC AAC GCA GTA GCA GTC CTC TAT TGT GTA CAT AAA NAT       48
Lys Ser Leu His Asn Ala Val Ala Val Leu Tyr Cys Val His Lys Xaa
                5                  10                  15

ATA ACA GTA CGA GAC ACC AAG GAA GCN TTA GAC AGG ATA GAG GAA GAA       96
Ile Glu Val Arg Asp Thr Lys Glu Ala Leu Asp Arg Ile Glu Glu Glu
            20                  25                  30

CAA AAC AAG TGT CAG CAA AAA ACA CAG CAG GCA AAA GAG GCT GAC GGA      144
Gln Asn Lys Cys Gln Gln Lys Thr Gln Gln Ala Lys Glu Ala Asp Gly
        35                  40                  45

AAA GTC AGT CAA                                                      156
Asn Val Ser Gln
    50
```

-continued

```
(2) INFORMATION FOR SEQ ID NO: 21:

     (i) SEQUENCE CHARACTERISTICS:
          (A) LENGTH:156 base pairs
          (B) TYPE:nucleic acid
          (C) STRANDEDNESS:single
          (D) TOPOLOGY:linear

    (ii) MOLECULE TYPE:genomic DNA

    (vi) ORIGINAL SOURCE:
          (A) ORGANISM:HIV ZAM20

  (viii) POSITION IN GENOME:213 to 381 of p17 gag protein

    (ix) FEATURE:
          (A) NAME/KEY:
          (B) LOCATION:1-156
          (C) IDENTIFICATION METHOD:established consensus sequence

    (xi) SEQUENCE DESCRIPTION:SEQ ID NO: 21:

AGA TCA TTA TAT AAC ACA GTA GCA ACT CTC TAT TGT GTA CAT GCA GGG       48
Arg Ser Leu Tyr Asn Thr Val Ala Thr Leu Tyr Cys Val His Ala Gly
                5                  10                  15

ATA GAG GTA CGA GAC ACC AAG GAA GCC TTA GAC GAG ATA GAG GAA GAA       96
Ile Glu Val Arg Asp Thr Lys Glu Ala Leu Asp Glu Ile Glu Glu Glu
            20                  25                  30

CAA AAC AAA TGT CAG CAA AAA ACA CAG CAG GCA AAA ACG GCT GAC GGA      144
Gln Asn Lys Cys Gln Gln Lys Thr Gln Gln Ala Lys Thr Ala Asp Gly
        35                  40                  45

AAG GTC AGT CAA                                                      156
Lys Val Ser Gln
    50


(2) INFORMATION FOR SEQ ID NO: 22:

     (i) SEQUENCE CHARACTERISTICS:
          (A) LENGTH:159 base pairs
          (B) TYPE:nucleic acid
          (C) STRANDEDNESS:single
          (C) TOPOLOGY:linear

    (ii) MOLECULE TYPE:genomic DNA

    (vi) ORIGINAL SOURCE:
          (A) ORGANISM:HIV DJ259

  (viii) POSITION IN GENOME:213 to 384 of p17 gag protein

    (ix) FEATURE:
          (A) NAME/KEY:
          (B) LOCATION:1-159
          (C) IDENTIFICATION METHOD:established consensus sequence

    (xi) SEQUENCE DESCRIPTION:SEQ ID NO: 22:

AGA TCA TTA TAT AAT ACA GTA GCA ACT CTC TAT TGT GTA CAT GCA AGG       48
Arg Ser Leu Tyr Asn Thr Val Ala Thr Leu Tyr Cys Val His Ala Arg
                5                  10                  15

ATA GAG ATA CAA GAC ACC AAA GAA GCA CTA GAC AAG ATA GAG GAA GAA       96
Ile Glu Ile Gln Asp Thr Lys Glu Ala Leu Asp Lys Ile Glu Glu Glu
            20                  25                  30

CAA AAC AAA TGT CAG CAA AAA ACA CAG AAG GCA GAA ACA GCT GAC AAG      144
Gln Asn Lys Cys Gln Gln Lys Thr Gln Lys Ala Glu Thr Ala Asp Lys
        35                  40                  45

GGA AAG GTC AGT CAA                                                  159
Gly Lys Val Ser Gln
    50

(2) INFORMATION FOR SEQ ID NO: 23:
```

-continued

```
     (i) SEQUENCE CHARACTERISTICS:
          (A) LENGTH:159 base pairs
          (B) TYPE:nucleic acid
          (C) STRANDEDNESS:single
          (D) TOPOLOGY:linear

    (ii) MOLECULE TYPE:genomic DNA

    (vi) ORIGINAL SOURCE:
          (A) ORGANISM:HIV VI313

  (viii) POSITION IN GENOME:213 to 384 of p17 gag protein

    (ix) FEATURE:
          (A) NAME/KEY:
          (B) LOCATION:1-159
          (C) IDENTIFICATION METHOD:established consensus sequence

    (xi) SEQUENCE DESCRIPTION:SEQ ID NO: 23:

ATA TCA TTA CAT AAT ACA GTA GCA ACT CTC TAT TGT GTA CAT GAG AAG       48
Ile Ser Leu His Asn Thr Val Ala Thr Leu Tyr Cys Val His Glu Lys
                5                   10                  15

ATA GAG ATA CGA GAC ACC AAG GAA GCC TTA GAC AAA ATA AAG GAA GAA       96
Ile Glu Ile Arg Asp Thr Lys Glu Ala Leu Asp Lys Ile Lys Glu Glu
            20                  25                  30

CAA AAC AAA AGT CAG CAA AAA ACA CAG CAG GCA GCA GCG GCT GAC AAT      144
Gln Asn Lys Ser Gln Gln Lys Thr Gln Gln Ala Ala Ala Ala Asp Asn
        35                  40                  45

GGA AAG GTC AGT CAA                                                  159
Gly Lys Val Ser Gln
    50


(2) INFORMATION FOR SEQ ID NO: 24:

     (i) SEQUENCE CHARACTERISTICS:
          (A) LENGTH:32 amino acids
          (B) TYPE:amino acid
          (C) TOPOLOGY:linear

    (ii) MOLECULE TYPE:peptide

    (vi) ORIGINAL SOURCE:
          (A) ORGANISM:HIV-1
          (B) STRAIN:HIV UG268

    (ix) FEATURE:
          (A) NAME/KEY:HIV UG268
          (B) LOCATION:1-32
          (C) IDENTIFICATION METHOD:established consensus sequence
          (D) OTHER INFORMATION:residues 9-40 of SEQ ID NO:8

    (xi) SEQUENCE DESCRIPTION:SEQ ID NO: 24:

Thr Leu Tyr Xaa Val His Lys Gly Ile Glu Val Arg Asp Thr Lys Glu
                5                   10                  15

Ala Leu Asp Lys Ile Glu Glu Glu Gln Asn Lys Ile Gln Gln Lys Thr
            20                  25                  30
```

HIV-1P-17 PEPTIDE FRAGMENTS, COMPOSITIONS CONTAINING AND METHODS FOR PRODUCING AND USING SAME

CROSS-REFERENCE TO RELATED APPLICATIONS

This application is a division of application Ser. No. 08/824,800, filed Mar. 26, 1997, now U.S. Pat. No. 6,111, 068 is a continuation-in-part of application Ser. No. 08/695, 301, filed Aug. 9, 1996 U.S. Pat. No. 6,093,400.

BACKGROUND OF INVENTION (1) Field of the Invention

This application is concerned with certain peptide fragments of the p-17 gag protein of human immunodeficiency virus (HIV), to compositions containing the peptide fragment and its use for therapeutic, including vaccine, and diagnostic purposes, to DNA coding for the peptide fragment, and to methods for producing and using the peptide fragments and DNA encoding the fragments.

More particularly, this invention relates to peptide fragments having from about 30 to about 50 amino acids and which correspond to the Consensus C lade (subtype) of the p-17 gag protein, namely, extending over the region inclusive of, depending on the particular strain, amino acids at positions 75 to 129, and DNA fragments encoding this region.

(2) Discussion of the Prior Art

There has been extensive research over the past several years, first to identify the cause of AIDS and, after the positive identification of the retroviruses generically referred to as HIV, as the causative organism, efforts have concentrated on more detailed analysis of the genetic makeup, molecular biology, pathogenesis, biochemistry, development of highly sensitive methods of detection of virus and antibodies and treatments, and therapies. Extensive progress has been made in all of these areas yet much work needs to be done to effectively combat the spread of AIDS. While the very recent development of combination therapies utilizing protease inhibitors has had substantial success as a therapeutic treatment it is still very expensive and not universally effective. Therefore, still an essential part of the approach for combatting the spread of the highly infectious HIV virus and treating the disease in already infected individuals is the development of effective vaccines and immunotherapeutic agents that stimulate the appropriate components of the immune system. In this regard, knowledge of natural history of infection with HIV and the various immune responses and the clinical condition and the outcome may be useful in preparing effective vaccine preparations for either therapy or prevention. In this regard accurate diagnosis of the stage of disease and the immune status with regard to HIV and the knowledge that certain modalities are available may encourage infected patients to alter or modify their lifestyles in such manner as to reduce the risk of spreading the virus. Additionally, identification of protective antibodies based on epitope recognition can offer a more effective mechanism for staging and/or diagnosing the AIDS or pre-AIDS disease. Such staging and early diagnosis of seropositive individuals may then allow for vaccinations to provide the appropriate protective immune responses for treating the seropositive individual.

In commonly assigned U.S. Pat. No. 4,983,387 to A. Goldstein and S. Wang, the patentees describe an antigenic peptide extending from at least about position 92 to about position 109 of p17 gag protein of HIV-1. More specifically, however, what is described in this patent is a triacontapeptide of the formula:

```
                                          (SEQ ID NO:3)
Tyr Ser Val His Gln Arg Ile Asp Val Lys Asp Thr

Lys Glu Ala Leu Glu Lys Ile Glu Glu Glu Gln Asn

Lys Ser Lys Lys Lys Ala.
```

(SEQ ID NO:3).

This triacontapeptide, referred to hereinafter as HGP-30, has shown positive results as a therapeutic agent against HIV, the causative organism of Acquired Immunodeficiency Deficiency Syndrome (AIDS) in certain clinical trials and in in vivo HIV challenge studies in SCID mice. One of the advantages of HGP-30, and the p-17 peptide, in general, is that this HIV protein tends to be more highly conserved across subtypes and strains of HIV than, for example, the envelope proteins. In fact, antibodies raised against HGP-30 in vaccinated individuals have been found by the present inventors to be recognized when tested against peptide sequences representing strains other than those represented by the HGP-30 sequence.

An interesting finding for HGP-30 is that this sequence contains both T and B cell epitopes immunoreactive with p17 of HIV (Sarin, et al., 1986, Science 232:1135; Naylor, et al., 1987, Proc. Nat. Acad. Sci. 84: 2951; Brander, et al., 1995, Clin. Exp. Immunol. 101:107–113; Dibrino, et al., 1994, J. Immunol. Vol. 154(2): 620–31). HGP-30 peptide has been conjugated to a large protein, Keyhole Limpet Hemocyanin (KLH), and found to be immunogenic in various animals and man, and the conjugate is well tolerated in both animals and humans (Gazzard, et al., 1992, Vaccine Res. 1:129; Sarin, et al., 1994, Vaccine Res. 3: 495; Kahn, et al., 1992, AIDS Res. Hu. Retroviruses 8:1321; Naylor, et al., 1991, Int. J. Immunopharm 13(Suppl): 117). A pilot study of HGP-30 vaccine has shown protection from HIV infection in such SCID Hu mice given PBMCs from an HGP-30 immunized donor (Sarin, et al., 1995, Cell. Molec. Biol. 41:401). More recently it has been shown that the presence of a predominance of IgG3 antibodies reactive to HGP-30 in sera of immunized human donors correlates with protection by PBMCs in the SCID Hu mouse HIV virus challenge model (Kahn et al 1996, Abstract 13 International AIDS Conference, Vancouver, Canada, July 1996; Talmadge, et al., 1996, Clin Immunol, Meeting New Orleans LA June 1996).

In particular, the sequence of HGP-30 is based on the HIV strain SF-2 which is a member of the B consensus sequence.

Prior work has established that p17 can be subdivided into several peptides for induction of immune responses (Goldstein, et al., U.S. Pat. No. 4,983,387; EP 0 246 829 Sarin, et al.; Jiang, et al., 1992, J. AIDS 5:382). That and other work has shown that in the p17 molecule numerous immunological epitopes are present for activities, such as B cell epitopes for induction of antibody, and T cell epitopes for helper activity and generation of cytotoxic T cells (Naylor, et al., 1990, Mono. Virol. 18:74; Coates, et al., 1987, Nature 326:549; Wahren, et al., 1989, J AIDS 4:448; Broliden, et al., ibid, Clin. Exp. Immunol. 76:216; Papsidero, et al., 1989, J. Virol 63:267; Boucher, et al., 1990, Clin. Lab. Anal. 4:43). Other work has shown that certain conjugates which include a T cell binding ligand (TCBL) and an epitope of interest from a disease associated antigen can also have biological activity even where the epitope alone is inactive (Zimmerman, et al., 1996a,b Vaccine Res. 5:91, 5:103; WO 89/12548).

It is difficult to predict whether changing the nature of a peptide, such as addition(s) or deletion(s) or substitution(s) of one or several amino acids, as occurs in different subtypes, could or would influence the subclass of antibody generated that recognize the epitope, even though it is known that such manipulations can induce different responses such as the stimulation of B and T cells, cytotoxic and lymphoproliferation responses. However, see our aforementioned U.S. Pat. No. 6,093,400, in which we demonstrated that a modified HGP-30 peptide, wherein the initial amino acid residue, corresponding to position 85, is shifted by at least 3 amino acid residues towards the N-terminal, i.e., beginning at the amino acid residue in the range of position 82 to 75 of the p17 gag peptide of HIV-1, induces a TH1 response. Nor is there evidence that the antibodies raised against a peptide fragment from one particular strain or subtype would exhibit different immunogenicity as compared to antibodies raised against corresponding peptide regions of other strains or subtypes.

It has now, surprisingly, been discovered, and this forms the basis of the present invention, that the peptide corresponding to HGP-30, but derived from Consensus C clade, elicits an even stronger and broad immune response than HGP-30 and, particularly, antibodies raised against a Consensus C sequence are able to recognize and give higher titers to HIV peptides from different subtypes and strains than antibodies to HGP-30.

Accordingly, it is an object of the invention to provide a novel peptide useful as a diagnostic aid for assaying for the HIV organism and/or as a prophylactic and therapeutic agent for treating AIDS or suppressing the formation of AIDS and having a T-cell epitope and, preferably also a B-cell epitope, and which has the ability to be recognized by antibodies raised against different subtypes and strains of HIV.

SUMMARY OF THE INVENTION

The above and other objects of the invention, which will become more readily apparent by the following detailed description and preferred embodiments and the accompanying drawing figures, are achieved by a peptide having from about 30 to about 50 consecutive amino acids taken from a part or the entirety of the following sequence:

```
                                        (SEQ ID NO:1)
1               5                   10
Xaa Ser Leu Xaa Asn Thr Val Xaa Xaa Leu Xaa Xaa

        15                  20
Val His Xaa Xaa Ile Xaa Xaa Xaa Asp Thr Lys Glu

25                  30                  35
Ala Leu Asp Xaa Xaa Xaa Glu Glu Gln Asn Lys Xaa

            40                  45
Gln Gln Lys Xaa Xaa Thr Xaa Xaa Xaa Xaa Xaa Ala

    50                  55
Asp Xaa Gly Xaa Val Ser Gln
```

wherein Xaa at position 1 is Arg, Lys or Ile;

Xaa at position 4 is Tyr, Phe or His;

Xaa at position 8 is Ala or Val;

Xaa at position 9 is Thr or Val;

Xaa at position 11 is Tyr or Trp;

Xaa at position 12 is Cys or Ser;

Xaa at position 15 is Lys, Glu, or Ala;

Xaa at position 16 is Gly, Lys, Asp, Glu, or Arg;

Xaa at position 18 is Glu or Thr;

Xaa at position 19 is Val or Ile;

Xaa at position 20 is Arg or Gln;

Xaa at position 28 is Lys, Arg or Glu;

Xaa at position 29 is Ile or Leu;

Xaa at position 30 is Glu or Lys;

Xaa at position 36 is Ile, Ser or Cys;

Xaa at position 40 is Thr or is a direct bond;

Xaa at position 41 is Lys or is a direct bond;

Xaa at position 43 is Gln or is a direct bond;

Xaa at position 44 is Gln, Lys or is a direct bond;

Xaa at position 45 is Ala or is a direct bond;

Xaa at position 46 is Lys, Glu or Ala;

Xaa at position 47 is Thr, Ala or Glu;

Xaa at position 50 is Lys, Asn, or a direct bond; and,

Xaa at position 52 is Lys or Gln.

In a particularly preferred embodiment the antigenic peptide has the sequence of SEQ ID NO: 2.

The invention also provides an immunologically active peptide comprising a peptide-carrier construct having the formula (I):

$$C^*—X—P^* \quad (I)$$

wherein

C* represents an immunogenic carrier material;

P* represents a peptide having SEQ ID NO:1; and

X represents a direct bond or covalent linkage linking the immunogenic carrier material C* and the peptide P*.

In another aspect, the invention provides a composition effective for eliciting a TH1 immune response when administered to a human patient in need thereof comprising an immunologically active peptide of the formula C*—X—P* as set forth above and an immune response adjuvant.

In another aspect, the invention provides a pharmaceutical composition containing a pharmacologically effective amount of a peptide of SEQ ID NO:1 and a pharmaceutically effective carrier.

In a particular aspect of the invention, there is provided an isolated nucleic acid molecule containing a nucleic acid sequence encoding for a peptide of SEQ ID NO:1.

In a preferred embodiment of this aspect of the invention, the isolated nucleic acid molecule contains a nucleic acid sequence having SEQ ID NO:16, SEQ ID NO:17, SEQ ID NO:18, SEQ ID NO:19, SEQ ID NO:20, SEQ ID NO:21, SEQ ID NO:22 or SEQ ID NO:23.

The present invention also provides a recombinant expression vector which includes at least one nucleic acid sequence encoding for a peptide of SEQ ID NO:1. The expression vector may be a eukaryotic expression vector or prokaryotic expression vector.

In still yet another aspect of the invention there is provided a host cell containing the recombinant vector as described above.

DETAILED DESCRIPTION OF THE INVENTION AND PREFERRED EMBODIMENTS

Figure 1:
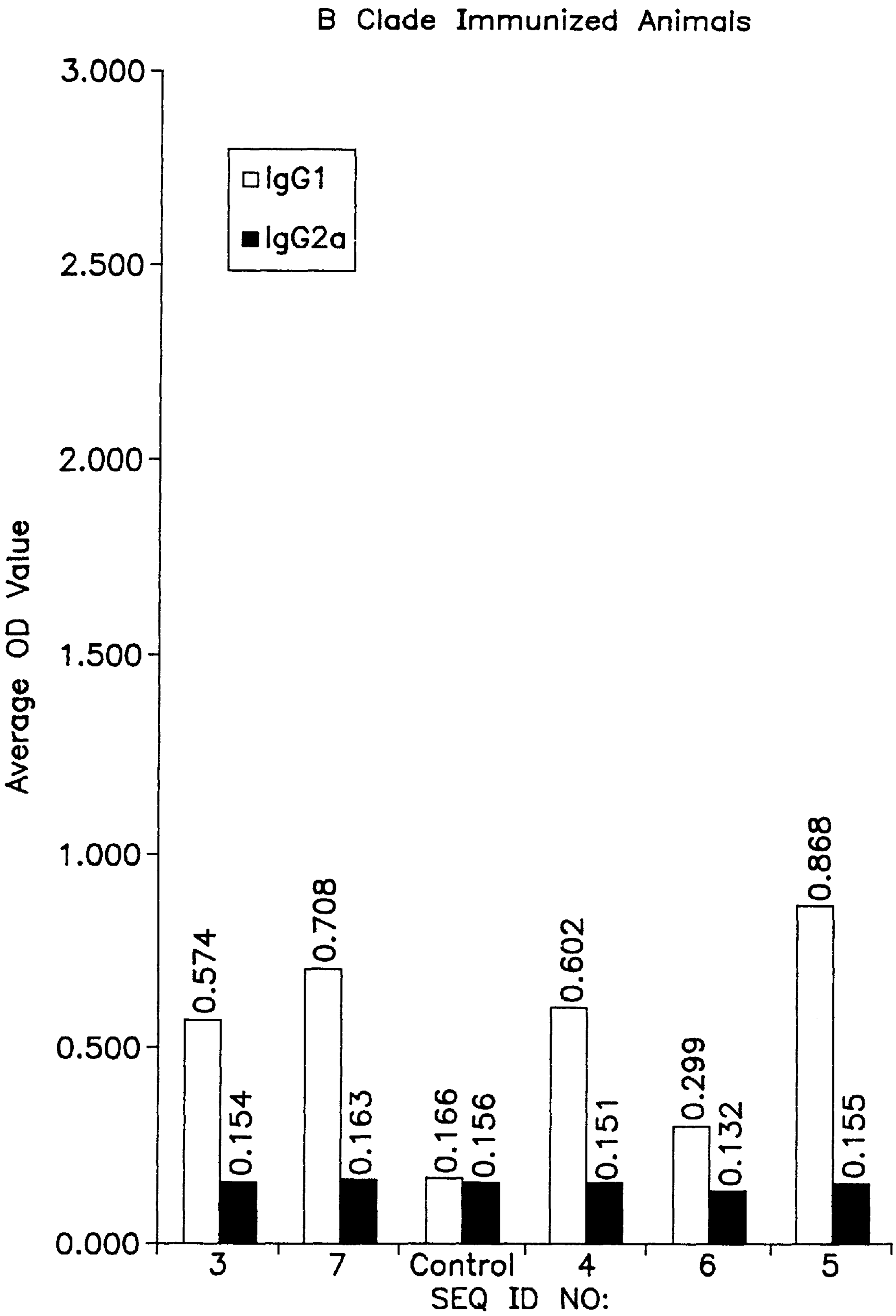
FIG. 1 is a graphical presentation of ELISA Assays for B Clade immunized animals against various peptides.

The ability of the antibodies or T cells induced by potential HIV vaccines to recognize other subtypes (also known as "clades") of HIV-1 has been problematic to date. For example, vaccines using envelope sequences induced antibodies recognize only closely related strains, due in part to the high polymorphism in the envelope proteins. The gag proteins, notably p17, being more highly conserved across strains and clades would, therefore, be more useful as vaccine antigens and as a diagnostic tool for worldwide use.

(QCB) (Hopkinton, Mass.) using the solid phase FMOC procedure and a double coupling protocol for the first 8 residues. The peptides were generally prepared with the carboxyl terminus as an amide form. All of the peptides were purified at QCB using preparative HPLC, and analyzed by an analytical HPLC and mass spectrometry. The peptides were greater than 95%, usually greater than 98%, pure by HPLC criteria and the mass was within 2 atomic mass units between lots and the expected value. The dry peptides obtained from QCB were stored in glass vials with desiccant at −20° C.

| Peptide Clade | Peptide Sequence (positions 86–115) |
|---|---|
| B<br>(Thailand B) | Y C V H Q K I E V K D T K E A L E K I E E E Q N K (SEQ ID NO:4)<br>S K K K A |
| C<br>(Uganda C) | Y C V H K G I E V R D T K E A L D K I E E E Q N K (SEQ ID NO:5)<br>I Q Q K T |
| E<br>(Thailand E) | W C V H Q R I E V K D T K E A L D K I E E V Q N K (SEQ ID NO:6)<br>S Q Q K T |
| HGP-30 | Y S V H Q R I D V K D T K E A L E K I E E E Q N K (SEQ ID NO:3)<br>S K K K A |

(Note: Thailand A Consensus sequence corresponds to Thailand E consensus sequence over this region of p17 including at least the amino acids at positions 85 to 114.)

Recent studies have shown HGP-30 to elicit both cellular and humoral immune responses. While some variation is seen within the amino acid sequences among subtypes and clades, significantly less variation within the p17 region corresponding to HGP-30 is seen than within the envelop sequences (10–30% vs. about 50%). In tests to be described below, antisera induced by an alum adjuvant formula of HGP-30 recognized HIV from the B and C subtypes and, to lesser extent, HIV-1 from E subtype. Other adjuvants yielded even better cross-species recognition.

Quite surprisingly, it has now been found that when similar tests were carried out but using antisera to the homologues of HGP-30 from the Consensus C, substantially stronger recognition to all types and classes of HIV subtypes is achieved.

Incidentally, as used herein, the terms "corresponding to" and "homologues of" and similar terms, when used in connection with and in reference to peptide fragments from different strains or subtypes, are intended to refer to peptide fragment sequences which, when the respective amino acid sequences of the protein strains containing the peptide fragments are matched or aligned, give the closest fit according to techniques well understood in the art.

The following tests were used to determine immunoreactivity of Anti-p17 Antisera to either HGP-30 (SEQ ID NO:3) or to homologous 30-mer peptides of the corresponding Consensus sequence from Clade C (SEQ ID NO:5), from Clade B (SEQ ID NO:4), from Clade E (SEQ ID NO:6) or to a modified HGP-30 (SEQ ID NO:7), or to a control peptide, as hereinafter defined.

Specifically, in order to demonstrate the cross-reactivity between various strains and subtypes (clades) of Human Immunodeficiency Virus (HIV) the following tests were carried out.

A. Peptide Synthesis.

The peptides that were used in these experiments were synthesized by Quality Controlled Biochemicals, Inc.

For the peptides disclosed above and below and as employed in the experimentation described herein, the amino acid sequences thereof, are set forth by the single identification letter symbol as follows:

| Amino Acid | Three-letter Symbol | One-letter abbreviation |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

B. Preparation of Conjugates

Keyhole Limpet Hemocyanin (KLH) (such as from Pierce, Rockford, Ill.) was conjugated to the peptide antigen by glutaraldehyde conjugation method (Naylor et al, 1987, Proc. Nat. Acad. Sci. 84:2951–5).

The conjugated KLH-peptides, dissolved in phosphate buffered saline (PBS), were analyzed for peptide using the BCA protein assay, and adjusted to contain between 200–400 μg/ml of total peptide, and stored at 4° C. in aliquots ready for use with an adjuvant.

C. Immunization, Anti-sera Collection and Processing

Groups (5–10 per group) of 10–16 week old BALB/c female mice (Taconic Farms, Germantown, N.Y.) were immunized and test bled according to the following schedule: immunizations on day 0, day 14; test bleedings on days 28 and 42.

The antigens were prepared with Alum (Pierce, Rockford, Ill.) adjuvant following the manufacturer's direction. The inoculum contained 25 μg of peptide (as KLH conjugate).

The mice were anesthetized by Metofane™ (Pitman-Moore, Mundelein, Ill.) for retroorbital bleeding and ear tagging. Blood from individual mice was collected on the specified days, processed to collect antisera and stored frozen until analysis by ELISA.

D. ELISA Assay

The sera was tested for the presence of antibody by an indirect ELISA (Zimmerman, et al., 1996, Vacc. Res. 5:103). The presence of antibodies specifically binding to HGP-30 (SEQ ID NO:3), Clade B (SEQ ID NO:4), Clade E (SEQ ID NO:6), Clade C (SEQ ID NO:5) or a modified Clade B HGP-30 (A T L Y S V H Q R I D V K D T K E A L E K I E E E Q N K S) (SEQ ID NO:7) (prepared as described above and also see our aforementioned application Ser. No. 08/695,301), or a control peptide, in the sample are assayed in an ELISA procedure. The control peptide, A, is derived from the HIV env, gp120 $V_3$ IIIB loop peptide 303–313 (Palker, et al., 1988, Proc. Nat. Acad. Sci. 85:1932–36). All peptides were coated at a concentration of 1 μg/ml.

The results obtained are shown in the following Tables C and D. From this data it is apparent that antibodies raised against HGP-30 recognize peptides of different sub-types (clades).

TABLE C

Immunoreactivity of anti-HGP-30 antisera (1:200 dilution) for peptides representing differing HIV Clades collected 28 days after Immunization on Days 0 and 7 with HGP-30-KLH in Alum

| | | PEPTIDE | | COATED | |
|---|---|---|---|---|---|
| | HGP-30 | Clade B | Clade E | Clade C | Control |
| Mouse # | | | | | |
| 854 | 0.950 | 0.927 | 0.135 | 0.840 | 0.069 |
| 855 | 0.396 | 0.308 | 0.083 | 0.724 | 0.057 |
| 856 | 0.940 | 0.894 | 0.220 | 0.949 | 0.066 |
| 857 | 0.780 | 0.642 | 0.146 | 0.820 | 0.065 |
| 858 | 0.686 | 0.612 | 0.200 | 0.804 | 0.059 |
| 859 | 0.724 | 0.617 | 0.303 | 0.854 | 0.073 |
| 860 | 0.832 | 0.801 | 0.159 | 0.905 | 0.077 |
| GROUP STD | 0.134 | 0.161 | 0.054 | 0.052 | 0.005 |
| GROUP MEAN | 0.758 | 0.686 | 0.178 | 0.842 | 0.066 |

Figure 2:
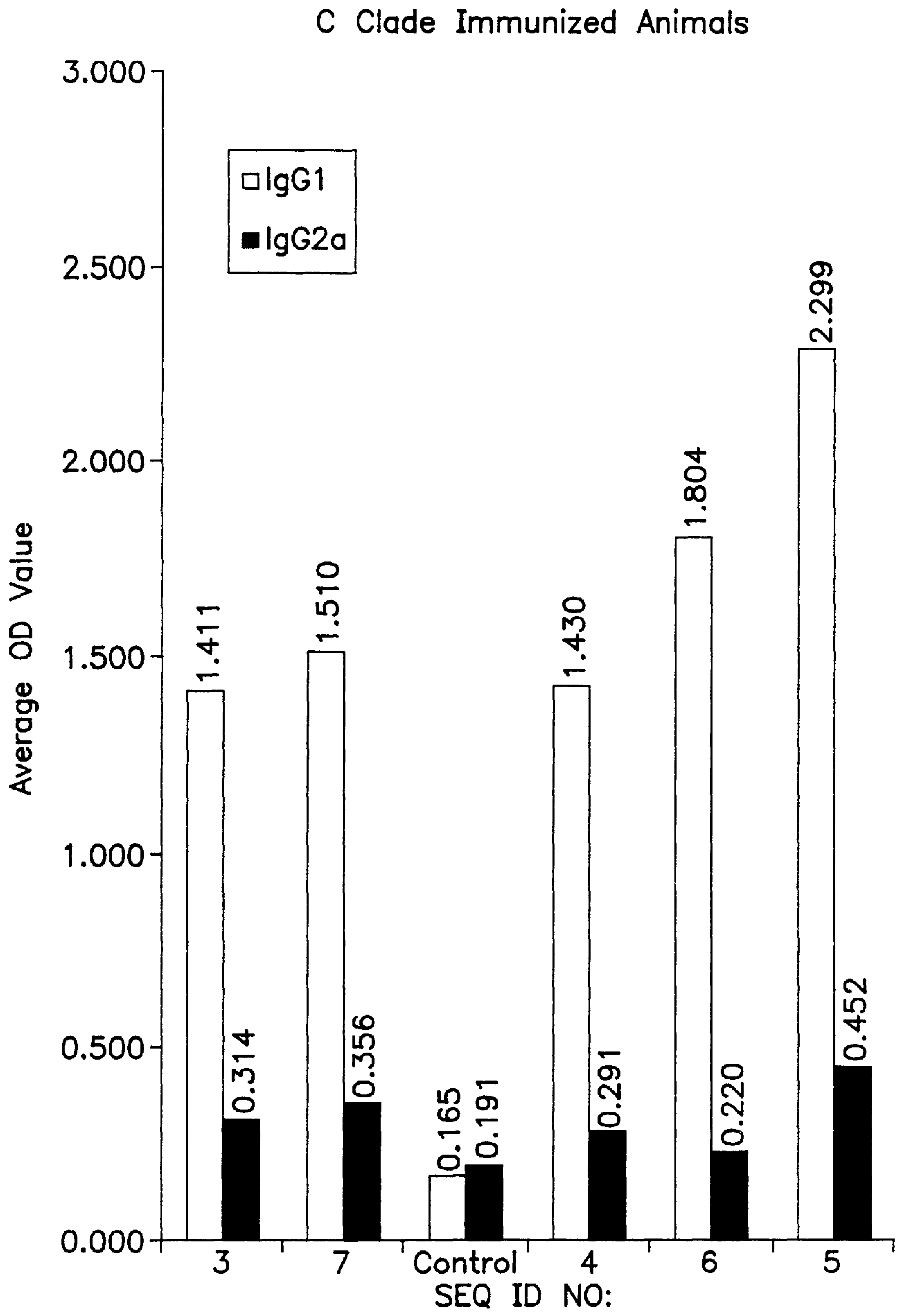
FIG. 2 is a graphical presentation of ELISA Assays for C Clade immunized animals against various peptides.
Figure 3:
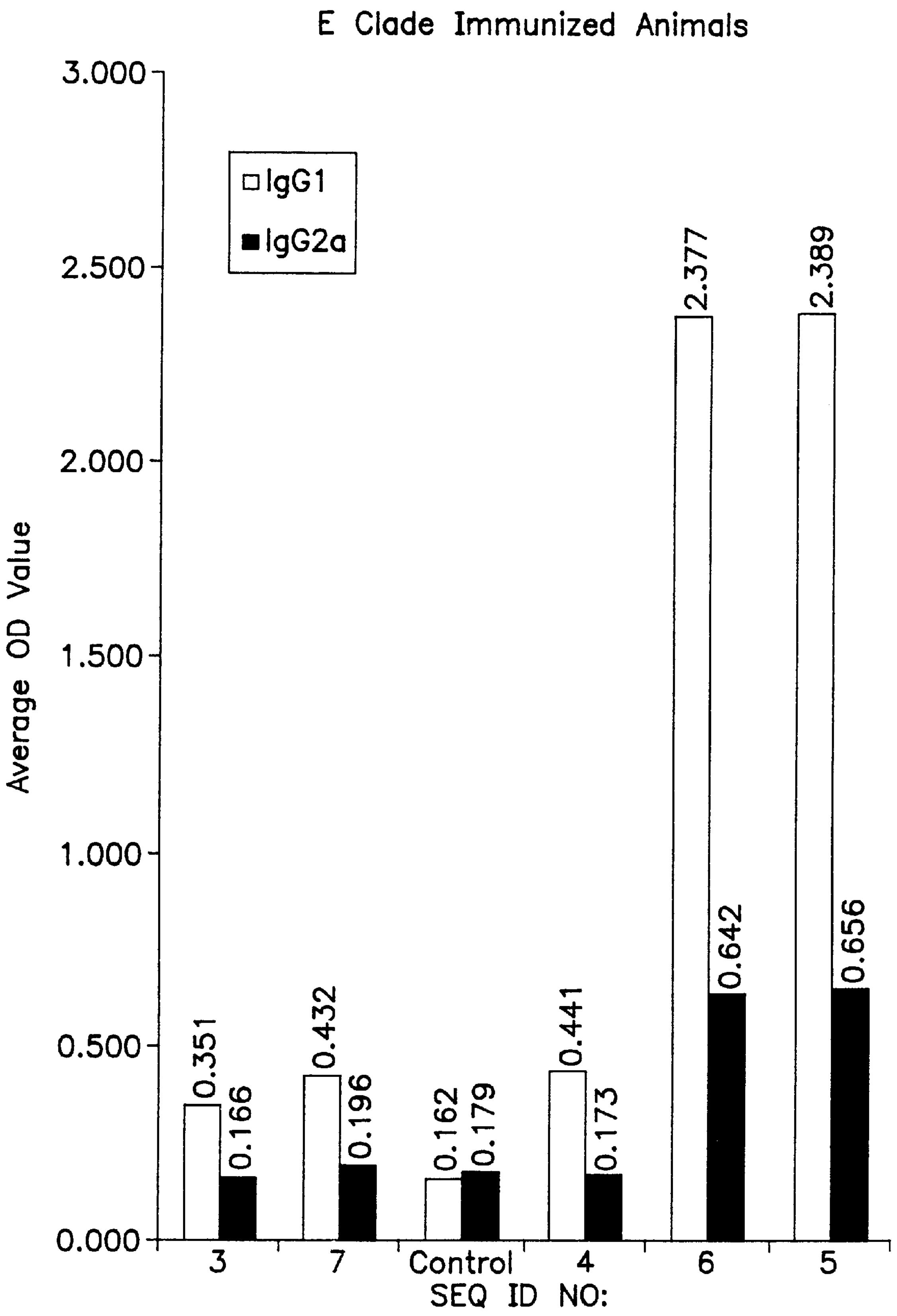
FIG. 3 is a graphical presentation of ELISA Assays for E Clade immunized animals against various peptides.

Using the same procedures as described above, except that the KLH used was Immucothel®, obtained from biosyn Arzneimittel GmbH, Fellbach, Germany, and the KLH-peptide conjugates, dissolved in PBS were adjusted to contain between 1 and 5 mg/ml of total peptide, and stored at 4° C., immunizations were carried to generate antibodies raised against the peptides described above for Clade B, Clade C and Clade E, conjugated to KLH as described above, and with Alum as adjuvant. ELISA Assays were carried out at a sample dilution of 1/200 for cross-reactivity with each of the antigenic peptides and also for the modified HGP-30 (mHGP-30) (SEQ ID NO:7). The results are shown graphically by the bar charts in FIGS. 1, 2 and 3 for the B Clade immunized mice, C clade immunized mice and E Clade immunized mice, respectively. In each case the results were obtained for different isotypes and are shown for IgG1 and IgG2a.

As before with antisera from HGP-30, the antisera to these different clades recognized the various antigenic peptides from different sub-types as well as over a different section of HIV in the case of the modified HGP-30. However, quite surprisingly, the C Clade peptide immunized mice exhibited substantially stronger immunogenic response as seen by comparing the results from FIG. 2 with the results from FIGS. 1 and 3.

Based on the results of the above tests it is apparent that the C Clade Consensus Sequence, which appears to be particularly prevalent in Africa and India, has an unexpectedly high probability of providing a broadly useful therapeutic or prophylactic agent in the arsenal against HIV as well as providing a powerful diagnostic tool capable of use in diagnostic assays around the world. Accordingly, any of the antigenic peptides which include the sequence beginning with the amino acid residue in the range of 75 to 85 and ending with the amino acid residue in the range of 114 to 128 of Consensus C Clade of p17 gag protein of HIV-1 and containing at least about 30 and up to about 50 amino acids, will be useful as immunogen in a vaccine or to produce antibodies or idiotypic antibodies and/or immune cellular responses directed against virus or viral infected cells useful in a vaccine for the purpose of inducing immunization or decreasing viremia associated with AIDS or as a component of a diagnostic assay or assay kit for the detection of the HIV virus.

The peptides according to the present invention are derived from Consensus C sequence of p17 gag peptide of HIV-1 and have from about 30 to about 50 consecutive amino acids taken from a part or the entirety of the following sequence

TABLE D

Immunoreactivity of anti-HGP-30 antisera (1:200 dilution) for peptides representing different HIV Clades collected at sequential times after Immunization with HGP-30-KLH

| Number of Mice Tested | Day of Test | Number of RESPONDERS* | | | |
|---|---|---|---|---|---|
| (Immunized) | Bleed | Clade B | Clade E | Clade C | HGP-30 |
| 7 | 14 | 3 (43%) | 1 (14%) | 6 (85%) | 5 (71%) |
| 7 | 28 | 7 (100%) | 3 (43%) | 7 (100%) | 7 (100%) |
| 6 | 42 | 6 (100%) | 4 (67%) | 6 (100%) | 6 (100%) |

*Reactivity is defined as signal being at least twice background (control wells) and ≧ 0.2, at a screening dilution of 1/200

In order to further demonstrate the cross-reactivity between the various strains of HIV the following additional experiments were carried out.

```
                                    SEQ ID NO:1
              5                   10
Xaa Ser Leu Xaa Asn Thr Val Ala Thr Leu Tyr Cys

        15                  20
Val His Xaa Xaa Ile Xaa Xaa Xaa Asp Thr Lys Glu

25                  30                  35
Ala Leu Asp Xaa Xaa Xaa Glu Glu Gln Asn Lys Xaa

            40                  45
Gln Gln Lys Xaa Xaa Thr Xaa Xaa Xaa Xaa Xaa Ala

    50                  55
Asp Xaa Gly Xaa Val Ser Gln
```

wherein Xaa at position 1 is Arg, Lys or Ile;

Xaa at position 4 is Tyr, Phe or His;

Xaa at position 8 is Ala or Val;

Xaa at position 9 is Thr or Val;

Xaa at position 11 is Tyr or Trp;

Xaa at position 12 is Cys or Ser;

Xaa at position 15 is Lys, Glu, or Ala;

Xaa at position 16 is Gly, Lys, Asp, Glu, or Arg;

Xaa at position 18 is Glu or Thr;

Xaa at position 19 is Val or Ile;

Xaa at position 20 is Arg or Gln;

Xaa at position 28 is Lys, Arg or Glu;

Xaa at position 29 is Ile or Leu;

Xaa at position 30 is Glu or Lys;

Xaa at position 36 is Ile, Ser or Cys;

Xaa at position 40 is Thr or is a direct bond;

Xaa at position 41 is Lys or is a direct bond;

Xaa at position 43 is Gln or is a direct bond;

Xaa at position 44 is Gln, Lys or is a direct bond;

Xaa at position 45 is Ala or Glu;

Xaa at position 46 is Lys, Glu or Ala;

Xaa at position 47 is Thr, Ala or Glu;

Xaa at position 50 is Lys, Asn, or a direct bond; and,

Xaa at position 52 is Lys or Gln.

Preferably, the peptide of this invention has from about 30 to about 33 consecutive amino acids corresponding to the following sequence:

```
                5                   10
Ala Thr Leu Tyr Cys Val His Xaa Xaa Ile Xaa Xaa

        15                  20
Xaa Asp Thr Lys Glu Ala Leu Asp Xaa Xaa Xaa Glu

25                  30                  35
Glu Gln Asn Lys Xaa Gln Gln Lys Xaa Xaa Thr
```

wherein Xaa at position 8 is Lys, Glu, or Ala;

Xaa at position 9 is Gly, Lys, Asp, Glu, or Arg;

Xaa at position 11 is Glu or Thr;

Xaa at position 12 is Val or Ile;

Xaa at position 13 is Arg or Gln;

Xaa at position 21 is Lys, Arg or Glu;

Xaa at position 22 is Ile or Leu;

Xaa at position 23 is Glu or Lys;

Xaa at position 29 is Ile, Ser or Cys;

Xaa at position 33 is Thr or is a direct bond; and

Xaa at position 34 is Lys or is a direct bond (SEQ ID NO:2).

Even more preferable is a peptide having SEQ ID NO:2 having from 30 to 32 amino acids and wherein the first amino acid in the sequence begins with the amino acid at from position 1 to 4, especially at position 1 or 2, and wherein Xaa at position 11 is Glu;

Xaa at position 12 is Val;

Xaa at position 13 is Arg;

Xaa at position 21 is Lys;

Xaa at position 22 is Ile;

Xaa at position 33 is a direct bond; and

Xaa at position 34 is a direct bond.

Specific examples of suitable C Clade peptide fragments beginning at position 75 (numbering for Consensus C) or position 76 (numbering for HIVUG268) to positions 125 to 129 of seven specific Consensus C strains of p17 of HIV-1 are shown in the following Table 1. The sequences reported in Table 1 and in the following Table 2 were taken from the report, "Human Retroviruses and AIDS 1994, A Compilation and Analysis of Nucleic Acid and Amino Acid Sequences" Edited by G. Myers, et al., Theoretical Biology and Biophysics, Group T-10, Los Alamos National Laboratory, Los Alamos, N. Mex.

TABLE 1

| Consensus.C | r | S | L | ? | N | t | V | a | t | L | y | C | V | H | ? | ? | I | e | v | r | D | T | K | E | A | L | D | k | i | e | E | E | Q | N | K | ? |
|---|---|---|---|---|---|---|---|---|---|---|---|---|---|---|---|---|---|---|---|---|---|---|---|---|---|---|---|---|---|---|---|---|---|---|---|---|
| HIVUG268 | - | - | - | Y | - | - | - | - | - | - | - | - | - | - | K | G | - | - | - | - | - | - | - | - | - | - | - | - | - | - | - | - | - | - | - | I |
| HIVSM145 | - | - | - | F | - | - | - | - | - | - | - | - | - | - | E | K | - | - | - | - | - | - | - | - | - | - | - | - | - | - | - | - | - | - | - | S |
| HIVZAM18 | K | - | - | F | - | - | - | V | - | - | W | - | - | - | E | D | - | T | - | - | - | - | - | - | - | - | - | R | L | - | - | - | - | - | - | S |
| HIVZAM19 | K | - | - | H | - | A | - | - | V | - | - | - | - | - | K | X | - | T | - | - | - | - | - | - | - | - | - | R | - | - | - | - | - | - | - | C |
| HIVZAM20 | - | - | - | Y | - | - | - | - | - | - | - | - | - | - | A | G | - | - | - | - | - | - | - | - | - | - | - | E | - | - | - | - | - | - | - | C |
| HIVDJ259 | - | - | - | Y | - | - | - | - | - | - | - | - | - | - | A | R | - | - | I | Q | - | - | - | - | - | - | - | - | - | - | - | - | - | - | - | C |
| HIVVI313 | I | - | - | H | - | - | - | - | - | - | - | - | - | - | E | K | - | - | I | - | - | - | - | - | - | - | - | - | K | - | - | - | - | - | - | S |

TABLE 1-continued

| | | |
|---|---|---|
| Consensus | C Q Q K ? ? T q q . . a k ? A D ? G k V S Q | (SEQ ID NO:8) |
| HIVUG268 | - - - . . - . . . . . E T - - K - - - - - | (SEQ ID NO:9) |
| HIVSM145 | - - - . . - - - . . - - A - - . - - - - - | (SEQ ID NO:10) |
| HIVZAM18 | - - - T K - - - . . - - A - - . - - - - - | (SEQ ID NO:11) |
| HIVZAM19 | - - - . . - - - . . - - E - - . Q - - - - | (SEQ ID NO:12) |
| HIVZAM20 | - - - . . - - - . . - - T - - . - - - - - | (SEQ ID NO:13) |
| HIVDJ259 | - - - . . - - K . . - E T - - K - - - - - | (SEQ ID NO:14) |
| HIVVI313 | - - - . . - - - . . - A A - - N - - - - - | (SEQ ID NO:15) |

In the above Table 1 the lower case letters represent sites of amino acid variability resulting from the allelic variations, genetic drift and mutations of the particular consensus sequence; the presence of a "?" symbol reflects that there is no agreed upon consensus for the amino acid at that position of the consensus sequence; the "dashes" (-) represent the same amino acid as set forth in the consensus sequence; and the "dots" (.) represent the absence of an amino acid at that position.

Furthermore, within the sequences in the above Table the partial fragments beginning at Ala at position 8 or at Thr at amino acid position 9 and extending for about 30 amino acids towards the C-terminal are especially preferred since these 30-mer peptide fragments include CTL as well as T-cell and B-cell epitopes.

As stated above the peptides of SEQ ID NO:1 are derived from the Clade C subtype of p17 protein of HIV-1 with the first amino acid residue in SEQ ID NO:1 corresponding to amino acid residue at position 75 or position 76. In this regard it is pointed out that the latter numbering is based on the sequence of the strain HIVUG268 of Clade C, while the former is based on the consensus sequence. However, not only is there some variation amongst HIV subtypes in the gag protein sequence, there is also differences in the specific numbering of amino acid residues among different HIV strains in the same subtype. It should be appreciated, therefore, that it is the amino acid sequence itself, allowing for variations observed amongst HIV subtypes, that is important, rather than the particular numbering of the native sequence.

It should also be understood that in any of the above amino acid sequences variations of specific amino acids, such as conservative amino acid substitutions, which do not adversely affect the desired biological activity are contemplated within the scope of the invention. In particular, it is recognized that the foregoing sequences are based upon a specific Clade of HIV, namely, Consensus C and, other naturally occurring and spontaneously occurring variants, within Consensus C, are included within the scope of the antigenic peptides of this invention. Such natural and spontaneously occurring amino acid variations are specifically contemplated for use in this invention. Moreover, in certain cases, it may be advantageous to use mixtures of peptides, at least one of the sequences of which fall within the guidelines given above and the other or others corresponding to other natural and spontaneously occurring variants of HIV; other sub-types of HIV and other regions of the p17 gag or other peptide fragment of HIV. Examples of such other peptides which may be used in combination with the antigenic peptides of this invention include, for example, HGP-30, modified HGP-30, peptides disclosed in the commonly assigned copending application Ser. No. 08/695,301, the disclosure of which is incorporated herein in its entirety by reference thereto; fragments from p24 protein of HIV-1; envelop proteins or peptide fragments, e.g., gp120, gp060, gp41 and the like.

As also recognized in the art when mixtures of two or more peptide fragments are used the different peptides may be linked directly to each other or linked via a known linking group or a spacer or linked to a common carrier, etc. Also, it is also known to link two or more of the same peptide fragments to each other directly or via a common carrier and this is also contemplated herein.

Still further, as well recognized in the art, it is often advantageous to make specific amino acid substitutions in order, for example, to provide specific binding sites or for purpose of radioactive or fluorescent tagging of the peptide. Such "designed" amino acid sequences are also within the scope of the antigenic peptides of this invention.

In addition to the variations in the amino acids among the various HIV strains, it is also recognized that the amino acids at the N-terminal and C-terminal may be present as the free acid (amino or carboxyl groups) or as the salts, esters, ethers, or amides thereof. In particular amide end groups at the C-terminal and acetylation, e.g., myristyl, etc. at the N- or C-terminal, are often useful without effecting the immunological properties of the peptide. Similarly, "chemical derivatives" wherein one or more of the amino acids are chemically derivatized by reaction of a functional side group will also generally fall within the scope of "conservative substitution" as long as the requisite activity is maintained or can be restored by reversing the chemical derivatization.

The peptides of the present invention can be prepared by conventional processes for synthesizing proteins, such as, for example, solid phase peptide synthesis, as described by Merrifield, R. B., 1963, J. of Am. Chem. Soc., 85:2149–2154, incorporated herein by reference thereto. It is also within the scope of the invention and within the skill in the art to produce the novel peptides of this invention by genetic engineering technology.

In the present invention, any of the antigenic Clade C peptide fragments may be used coupled to an immunogenic carrier material to produce an antigenic peptide-carrier construct. Generally, natural and synthetic proteins having a high molecular weight which are conventionally employed in the preparation of antigens can be employed as the immunogenic carrier material. In addition, however, smaller peptides or molecules, such as tuftsin (a tetrapeptide), analogs of tuftsin, and muramyl dipeptides, and its analogs, can also be used as "immunogenic carrier materials."

As used herein the term "immunogenic carrier material" is meant to include those materials which have the property of independently eliciting an immunogenic response in a host animal and which can be covalently coupled to peptide either directly via a formation of peptide or ester bonds between free carboxyl, amino or hydroxyl groups in the polypeptide and corresponding groups on the immunogenic carrier material or alternatively by bonding through a conventional bifunctional linking group. Examples of such carriers include albumins of animal sera such as horse serum albumin, bovine serum albumin, rabbit serum albumin, human serum albumin, sheep serum albumin, etc.; globulins of animal sera such as horse serum globulin, bovine serum globulin, rabbit serum globulin, human serum globulin, sheep serum globulin, etc.; thyroglobulins of animals such as horse thyroglobulin, human thyroglobulin, sheep thyroglobulin, etc.; hemoglobulins of animals such as horse hemoglobulin, bovine hemoglobulin, rabbit hemoglobulin, human hemoglobulin, sheep hemoglobulin, etc.; hemocyanins of animals such as Keyhole limpet hemocyanin (KLH), etc.; proteins extracted from ascaris (ascaris extracts, such as those described in Japanese Patent Application (OPI) No. 16,414/81, *J. Immun.,* 111, 260–268 (1973), ibid., 122, 302–308 (1979), ibid. 98, 893–900 (1967) and *Am. J. Physiol.,* 199, 575–578 (1960), or purified products thereof); polylysine, polyglutamic acid, lysine-glutamic acid copolymers, copolymers containing lysine or ornithine, etc. Recently, vaccines have been produced using diphtheria toxoid or tetanus toxoid as immunogenic carrier materials (see Lepow, M. L., et al., *J. of Infectious Diseases,* Vol. 150, No. 3, page 402–406 (1984); and Coen Beuvery, E., et al. *Infection and Immunity* 40, pages 39–45 (April 1983) and these toxoid materials can also be used herein. Still other suitable toxoid materials include cholera, PPD, bordetella pertussis, and the like. Other suitable carriers are disclosed in, for example, U.S. Pat. No. 4,575,495, including vaccines, organic polymers, etc.

As hapten-carrier linking agents, those conventionally employed in the preparation of antigens can be widely employed. Specific examples of these agents include diazonium compounds for crosslinking tyrosine, histidine, tryptophan, etc., e.g. bisdiazotized benzidine (BDB), etc.; aliphatic dialdehydes for crosslinking an amino group with an amino group, e.g. $C_2$–$C_7$ alkanals, such as glyoxal, malonedialdehyde, glutaraldehyde, succinaldehyde, adipaldehyde, etc.; dimaleimide compounds for crosslinking a thio group with a thio group, e.g. N,N'-o-phenylenedimaleimide, N,N'-m-phenylenedimaleimide etc.; maleimidocarboxyl-N-hydroxysuccinimide ester for crosslinking an amino group with a thiol group, e.g. metamaleimidobenzoyl-N-hydroxysuccinimide ester, 4-(maleimidomethyl)-cyclohexane-1-carboxyl-N'-hydroxysuccinimide ester, etc.; agents used in conventional peptide bond forming reactions in which amide bonds are formed from an amino group and a carboxyl group, e.g. dehydrating and condensing agents such as carbodiimides, e.g. N,N-dicyclohexylcarbodiimide, N-ethyl-N'-dimethylaminocarbodiimide, 1-ethyl-3-diisopropylaminocarbodiimide, 1-cyclohexyl-3-(2-morpholinyl-4-ethyl)carbodiimide, etc. As the foregoing hapten-carrier linking agent, it is also possible to use diazonium aryl carboxylic acids such as p-diazonium phenylacetic acid, etc., with conventional peptide bond forming agents such as the dehydrating and condensing agents described above in combination.

The covalent coupling of the invention peptide to the immunogenic carrier material can be carried out in a manner well known in the art. Thus, for example, for direct covalent coupling it is possible to utilize a carbodiimide, most preferably dicyclohexylcarbodiimide or 1-ethyl-3-(3-dimethylamino-propyl)carbodiimide as coupling agent. In such direct coupling it is desirable to utilize a slightly acidic reaction medium for this step, e.g. a medium having a pH in the range of from about 3 to 6.5, most preferably in the range of from about 4 to 6.5.

The coupling reaction for preparing antigens using as haptenes those peptides that are neutral or alkaline can be carried out in similar manner but in an aqueous solution or conventional buffer solution having pH of 7 to 10, preferably in a buffer solution having pH of 8 to 9, at temperatures of about 0° to 40° C., preferably around room temperature. The reaction is generally completed within about 1 to about 24 hours, preferably 13 to 15 hours. Representative examples of buffer solutions which can be used in the above process include:

0.2 sodium hydroxide-0.2M boric acid 0.2M potassium chloride buffer solution;

0.2M sodium carbonate-0.2M boric acid 0.2M potassium chloride buffer solution;

0.05M solution tetraborate-0.2M boric acid 0.2M sodium chloride buffer solution;

0.1M dihydrogen potassium phosphate 0.05M sodium tetraborate buffer solution.

In the above, proportions of the hapten, hapten-carrier linking agent and carrier can be appropriately determined but it is preferred that the hapten be employed in an amount of about 1 to about 10 times, preferably about 1 to about 5 times, the weight of the hapten and the hapten-carrier linking agent be employed in an amount of about 5 to about 10 times the mol of the hapten. By the above reaction, the carrier is bound to the hapten via the hapten-carrier linking agent to obtain a desired antigen composed of a peptide-carrier complex.

After completion of the reaction, the thus obtained antigen can easily be isolated and purified by means of a dialysis method, a gel filtration method, a fractionation precipitation method, etc.

The thus obtained antigen contains 50 to 600 mols on average of the peptide thereto per mole of a protein and enables one to subsequently prepare an antibody having a high specificity to the antigen. Particularly, antigens to which the peptide is bound in an amount of 50 to 200 mols, preferably 80 to 200 mols, on average, per mol of a protein are preferred since they have higher specificity and enable one to obtain antibodies having high activity and sensitivity.

The peptide-carrier constructs according to the invention may be broadly represented by the formula (I):

$$C^*\text{—}X\text{—}P^* \qquad (I)$$

where C* represents an immunogenic carrier material, as defined above;

P* represents a Clade C peptide fragment of from about 30 to about 50 amino acids, corresponding to SEQ ID NO:1; and X represents a direct bond or covalent linkage linking the immunogenic carrier C* and peptide P*.

Any of the known methods for forming peptide constructs can be used in this invention. For instance, using a method adapted from Ziegers, et al., 1990, J. Immunol. Meth., 130:195–200, the antigenic Clade C peptide is coupled to KLH or other suitable immunogenic carrier material by activating the KLH by dialysis against 0.2% glutaraldehyde in PBS for 16 hours at 4° C. followed by dialysis against PBS (3 times, 500 ml each). The peptide is added to the activated KLH (100:1 molar ratio) and the mixture is stirred at 4° C. for 16 hours. Lysine is added to a final concentration of 20 mM to block the unreacted activated KLH and stirred for 2 hours at 4° C. Excess peptide and lysine are dialyzed against PBS (2 times; 200 ml ea) at 4° C.

In addition to peptide constructs as described above it is also possible to use the antigenic Clade C peptides of this invention in the form of a heterofunctional immunological conjugate in the place of the T cell specific binding ligand which is an antigenic peptide capable of eliciting TH1 associated antibodies as described in our copending application Ser. No. 08/695,304, the disclosure of which is incorporated herein in its entirety by reference thereto.

While the peptide-carrier constructs may be used without any other antigenic compound or immune system biological response modifier it may often be advantageous to take a "cocktail" approach in an AIDS therapy, whether as a prophylactic treatment or therapeutic treatment. Accordingly, it is also within the scope of the invention to combine the antigenic peptide of SEQ ID NO:1, as such, or as the peptide-carrier construct of formula (I), heterofunctional immunological conjugate with another antigenic material. Such other antigenic material may be selected from among any of the known or hereinafter discovered antigenic materials containing one or more epitopes effective for eliciting a cytotoxic T lymphocyte (CTL) response or T helper (Th) response and which are derived from or based on any of the gag, e.g. p7, p17, p24; env, e.g. gp120, gp160, gp41, or pol proteins of HIV-1, many of which are already well known to those skilled in the art.

In such compositions the Clade C antigenic peptide or peptide-carrier construct or heterofunctional immunological construct of the invention may be administered with the other antigenic material in a single composition or as separate formulations administered in combination. Furthermore, the Clade C antigenic peptide or peptide-carrier construct heterofunctional conjugate may also be linked directly to each other or via a suitable linking group, as also well known in the art.

In another aspect of the invention, instead of the above described peptide fragments, or peptide-carrier constructs or heterofunctional immunological conjugate or mixture of peptide fragment or peptide-carrier construct or heterofunctional immunological conjugate with another antigenic material there may be provided the corresponding DNA sequence encoding for such peptides or constructs or conjugates or mixtures thereof. These nucleic acid sequences may, in turn, be bonded to appropriate initiation, termination, promoter sequences, etc., as is well known in the art. In this regard, it may be advantageous in some treatment strategies to administer to a patient in need thereof the DNA sequence coding for the peptide of SEQ ID NO:1 or any of the peptides of SEQ ID NO's 2 to 15. Of course, as well known in the art the DNA sequences may be used for the production of the corresponding encoded peptide by any of the conventional genetic engineering techniques.

Therefore, the invention contemplates an isolated nucleic acid molecule (DNA) which includes a nucleic acid sequence encoding for a peptide according to the invention.

The DNA consensus sequence for Clade C peptide of SEQ ID NO:8 is set forth below and also in the following Table 2:

```
aga tca tta tat aac aca gta gca act ctc tat tgt gta cat gaa  45 (SEQ ID NO:16).
?ag ata gag gta cga gac acc aag gaa gcc tta gac aag ata gag  90
gaa gaa caa aac aaa agt cag caa aaa ??? ??? aca cag cag gca 135
aaa gcg gct gac ??? gga aag gtc agt caa.                    165
```

The following Table 2 sets forth the DNA sequences which code for the peptides identified as SEQ ID NO's 9 to 15 as well as the consensus sequence for SEQ ID NO:8. However, it is understood by those skilled in the art that there is degeneracy in the genetic code, i.e., the code is redundant in most cases, and that most of the codons set forth in the following Table 2 can be replaced by another codon corresponding to the particular amino acid. For example, Leucine (Leu or L) is coded for by the following nucleotide triplets (codons): TTT and TTC; Threonine (Thr or T) is coded for by ACT, ACC, ACA, and ACG; Lysine (Lys or K) is coded for by AAA and AAG, and so on, where the nucleotide bases A, C, G, and T represent, adenine, cytosine, guanine and thymine, respectively. Such DNA sequences containing one or more variations in nucleic acid sequences but, which will still result in a DNA sequence capable of encoding the antigenic peptides described herein, are functionally equivalent to the sequences as set forth below and are intended to be encompassed by the invention.

TABLE 2

| Consensus C | AgA | TCA | TTA | tat | AAc | aCA | GTA | GcA | act | CTc | Tat | TGT | GTA | CAT | gaa | ?ag | ATA | gag | gTA |
|---|---|---|---|---|---|---|---|---|---|---|---|---|---|---|---|---|---|---|---|
| HIVUG268 | --- | --- | --- | --- | --- | --- | --- | --- | --- | --- | --- | --- | --- | --- | A-- | GG- | --- | --- | A-- |
| HIVSM145 | --- | --- | --- | -TC | --- | --- | --- | --- | --- | --- | --- | --- | --- | --- | --- | A-- | --- | --- | --- |
| HIVZAM18 | -A- | --- | --- | -TC | --- | --- | --- | -T- | --- | --A | -GG | --- | --- | --- | --- | G-T | --- | ACA | --- |
| HIVZAM19 | -A- | --- | --- | C-C | --- | G-- | --- | --- | --- | GTC | --- | --- | --- | --- | A-- | N-T | --- | ACA | --- |
| HIVZAM20 | --- | --- | --- | --- | --- | --- | --- | --- | --- | --- | --- | --- | --- | --- | -C- | GG- | --- | --- | --- |
| HIVDJ259 | --- | --- | --- | --- | --T | --- | --- | --- | --- | --- | --- | --- | --- | --- | -C- | AG- | --- | --- | A-- |
| HIVVI313 | -T- | --- | --- | C-- | --T | --- | --- | --- | --- | --- | --- | --- | --- | --- | --G | A-- | --- | --- | A-- |

TABLE 2-continued

| | | | | | | | | | | | | | | | | | | | |
|---|---|---|---|---|---|---|---|---|---|---|---|---|---|---|---|---|---|---|---|
| Consensus.C | CgA | GAC | ACC | AAg | GAA | GCc | tTA | GAC | aag | aTA | gAG | GAA | GAA | CAA | AAC | AAa | agT | CAG | CAA |
| HIVUG268 | --- | --- | --- | --- | --- | --- | --- | --- | --- | --- | --- | --- | --- | --- | --- | --G | -T- | --- | --- |
| HIVSM145 | --- | --- | --- | --- | --- | --- | --- | --- | --- | --- | --- | --- | --- | --- | --- | --- | --- | --- | --- |
| HIVZAM18 | --- | --- | --- | --- | --- | --- | --- | --- | -G- | T-- | --- | --- | --- | --- | --- | --- | --- | --- | --- |
| HIVZAM19 | --- | --- | --- | --- | --- | --N | --- | --- | -G- | --- | --- | --- | --- | --- | --- | --G | T-- | --- | --- |
| HIVZAM20 | --- | --- | --- | --- | --- | --- | --- | --- | G-- | --- | --- | --- | --- | --- | --- | --- | T-- | --- | --- |
| HIVDJ259 | -A- | --- | --- | --A | --- | --A | C-- | --- | --- | --- | --- | --- | --- | --- | --- | --- | T-- | --- | --- |
| HIVVI313 | --- | --- | --- | --- | --- | --- | --- | --- | --A | --- | A-- | --- | --- | --- | --- | --- | --- | --- | --- |

| | | | | | | | | | | | | | | | | | | |
|---|---|---|---|---|---|---|---|---|---|---|---|---|---|---|---|---|---|---|
| Consensus.C | AAA | ??? | ??? | ACA | cag | cag | GcA | aaA | gcg | gct | GAC | ??? | GGA | aAg | GTC | AGT | CAA | (SEQ ID NO:16) |
| HIVUG26B | --- | ... | ... | --- | ... | ... | -A- | -C- | --T | ... | --- | AAA | --- | --- | --- | --- | --- | (SEQ ID NO:17) |
| HIVSM145 | --- | ... | ... | --- | --- | --- | --- | --- | --- | --- | --- | ... | --- | --- | --- | --- | --- | (SEQ ID NO:18) |
| HIVZAM18 | --- | ACA | AAA | --- | --- | --- | --- | --- | --- | --- | --- | ... | --- | C-- | --- | --- | --- | (SEQ ID NO:19) |
| HIVZAM19 | --- | ... | ... | --- | --- | --- | --- | --- | -A- | --- | --- | ... | --- | --A | --- | --- | --- | (SEQ ID NO:20) |
| HIVZAM20 | --- | ... | ... | --- | --- | --- | --- | --- | -A- | --- | --- | ... | --- | --- | --- | --- | --- | (SEQ ID NO:21) |
| HIVDJ259 | --- | ... | ... | --- | --- | A-- | --- | G-- | A-A | --- | --- | AAG | --- | --- | --- | --- | --- | (SEQ ID NO:22) |
| HIVVI313 | --- | ... | ... | --- | --- | --- | --- | GC- | --- | --- | --- | AAT | --- | --- | --- | --- | --- | (SEQ ID NO:23) |

In the above Table 2, similarly to Table 1, the lower case letters represent sites of nucleic acid variability resulting from the allelic variations, genetic drift and mutations of the particular consensus sequence; the presence of a "?" symbol reflects that there is no agreed upon consensus for the nucleotide at that position of the consensus sequence; the "dashes" (-) represent the same nucleotide as set forth in the consensus sequence; and the "dots" (.) represent the absence of a nucleotide at that position. It is recognized that the foregoing sequences are based upon a specific Clade of HIV, namely, Consensus C and, other naturally occurring and spontaneously occurring variants, within Consensus C, are included within the scope of the nucleic acid sequences encoding for the antigenic peptides and peptide-carrier constructs of this invention.

The DNA sequences coding for the peptides of this invention can be prepared by any of the well known techniques for recombinant gene technology. For example, reference can be made to the disclosure of recombinant HIV (HTLV-III) proteins and peptides in U.S. Pat. No. 5,142,024 and the body of literature mentioned therein, and the disclosures of which are incorporated herein by reference thereto.

Thus, this invention also provides a recombinant DNA molecule comprising all or part of the nucleic acid sequence encoding the antigenic peptide of this invention or the peptide-carrier construct of formula (I) and a vector. Expression vectors suitable for use in the present invention comprise at least one expression control element operationally linked to the nucleic acid sequence. The expression control elements are inserted in the vector to control and regulate the expression of the nucleic acid sequence. Examples of expression control elements include, but are not limited to, lac system, operator and promoter regions of phage lambda, yeast promoters and promoters derived from polyoma, adenovirus, cytomegalovirus, retrovirus or SV40. Additional preferred or required operational elements include, but are not limited to, leader sequence, termination codons, polyadenylation signals and any other sequences necessary or preferred for the appropriate transcription and subsequent translation of the nucleic acid sequence in the host system. It will be understood by one skilled in the art that the correct combination of required or preferred expression control elements will depend on the host system chosen. It will further be understood that the expression vector should contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods (see, e.g., Ausubel, et al., (1987) in "Current Protocols in Molecular Biology", John Wiley and Sons, New York, N.Y.) or are commercially available.

Another aspect of this invention relates to a host organism into which a recombinant expression vector containing all or part of the nucleic acid sequence encoding for an antigenic peptide of the invention, or the peptide-carrier construct of formula (I) has been inserted. The host cells transformed with the nucleic acid sequences encompassed by this invention include eukaryotes, such as animal, plant, insect and yeast cells and prokaryotes, such as *E. coli.* The means by which the vector carrying the gene may be introduced into the cell include, but are not limited to, microinjection, electroporation, transduction, or transfection using DEAE-dextran, lipofection, calcium phosphate or other procedures known to one skilled in the art (see, e.g., Sambrook, et al. (1989) in "Molecular Cloning. A Laboratory Manual", Cold Spring Harbor Press, Plainview, N.Y.).

In a preferred embodiment of this aspect, eukaryotic expression vectors that function in eukaryotic cells are used. Examples of such vectors include, but are not limited to, retroviral vectors, vaccinia virus vectors, adenovirus vectors, herpes virus vector, fowl pox virus vector, plasmids, such as pCDNA3 (Invitrogen, San Diego, Calif.) or the baculovirus transfer vectors. Preferred eukaryotic cell lines include, but are not limited to, COS cells, CHO cells, HeLa cells, NIH/3T3 cells, 293 cells (ATCC# CRL1573), T2 cells, dendritic cells, monocytes or Epstein-Barr virus transformed B cells. Mammalian cells, such as NIH/3T3, COS-7, CHO, 293 cells (ATCC #CRL 1573), T2 cells, dendritic cells, or monocytes are generally preferred to ensure proper processing and modification of the protein.

The recombinant protein expressed by the host cells can be obtained as a crude lysate or can be purified by standard protein purification procedures known in the art which may include differential precipitation, molecular sieve chromatography, ion-exchange chromatography, isoelectric focusing, gel electrophoresis, affinity, and immunoaffinity chromatography and the like. (see, e.g., Ausubel, et al., (1987) in "Current Protocols in Molecular Biology" John Wiley and Sons, New York, N.Y.). In the case of immunoaffinity chromatography, the recombinant protein may be purified by passage through a column containing a resin which has bound thereto antibodies specific for the antigenic peptide (Ausubel, et al., (1987) in "Current Protocols in Molecular Biology" John Wiley and Sons, New York, N.Y.). The isolated protein may be further purified by HPLC or other purification method.

The antigenic peptides of this invention, or peptide-carrier constructs thereof, may be used as a vaccine either prophylactically or therapeutically. When provided prophylactically the vaccine is provided in advance of any evidence of virus infection. The prophylactic administration of the invention vaccine should serve to prevent or attenuate AIDS in a mammal. In a preferred embodiment a human, at high risk for AIDS is prophylactically treated with a vaccine of this invention. When provided therapeutically, the vaccine is provided to enhance the patient's own immune response to the HIV antigen. The vaccine, which acts as an immunogen, may be a cell, cell lysate from cells transfected with a recombinant expression vector encoding for the antigenic peptide or peptide-carrier construct, or a culture supernatant containing the expressed protein. Alternatively, the immunogen is a partially or substantially purified recombinant protein, peptide or analog thereof encoding for the peptide or peptide-carrier construct of the invention.

While it is possible for the immunogen to be administered in a pure or substantially pure form, it is preferable to present it as a pharmaceutical composition, formulation or preparation.

The formulations of the present invention, both for clinical and for human use, comprise an immunogen as described above, together with one or more pharmaceutically acceptable carriers and, optionally, other therapeutic ingredients. The carrier(s) must be "acceptable" in the sense of being compatible with the other ingredients of the formulation and not deleterious to the recipient thereof. The formulations may conveniently be presented in unit dosage form and may be prepared by any method well-known in the pharmaceutical art.

All methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for intravenous, intramuscular, subcutaneous, or intraperitoneal administration conveniently comprise sterile aqueous solutions of the active ingredient with solutions which are preferably isotonic with the blood of the recipient. Such formulations may be conveniently prepared by suspending or dissolving solid active ingredient in water containing physiologically compatible substances such as sodium chloride (e.g. 0.1–2.0M), glycine, and the like, and having a buffered pH compatible with physiological conditions to produce an aqueous solution or suspension, and rendering the solution sterile. These may be present in unit or multi-dose containers, for example, sealed ampoules or vials.

The formulations of the present invention may incorporate a stabilizer. Illustrative stabilizers are polyethylene glycol, proteins, saccharides, amino acids, inorganic acids, and organic acids which may be used either on their own or as admixtures. These stabilizers, when used, are preferably incorporated in an amount of about 0.1 about 10,000 parts by weight per part by weight of immunogen. If two or more stabilizers are to be used, their total amount is preferably within the range specified above. These stabilizers are used in aqueous solutions at the appropriate concentration and pH. The specific osmotic pressure of such aqueous solutions is generally in the range of about 0.1 to about 3.0 osmoles, preferably in the range of about 0.8 to bout 1.2. The pH of the aqueous solution is adjusted to be within the range of about 5.0 to about 9.0, preferably within the range of 6–8. In formulating the immunogen of the present invention, anti-adsorption agent may be used.

Additional pharmaceutical methods may be employed to control the duration of action. Controlled release preparations may be achieved through the use of polymer to complex or absorb the proteins or their derivatives. The controlled delivery may be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the peptide or peptide-carrier construct into particles of a polymeric material such as, for example, polyesters, polyamino acids, hydrogels, poly(lactic acid), polyglycolic acid, copolymers of these acids, or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxy-methylcellulose or gelatin-microcapsules and poly (methylmethacrylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined with typical carriers, such as lactose, sucrose, starch, talc, magnesium stearate, crystalline cellulose, methyl cellulose, carboxymethyl cellulose, glycerin, sodium alginate or gum arabic among others.

The peptides of the present invention may be supplied in the form of a kit, alone, or in the form of a pharmaceutical composition as described above.

Vaccination can be conducted by conventional methods. For example, the immunogen can be used in a suitable diluent such as saline or water, or complete or incomplete adjuvants. Further, the immunogen may or may not be bound to a carrier to make the protein immunogenic or enhance the protein's immunogenecity. Examples of such carrier molecules include but are not limited to bovine serum albumin (BSA), keyhole limpet hemocyanin (KLH), tetanus toxoid, and the like. The immunogen also may be coupled with lipoproteins, lipids or fatty acids or administered in liposomal form or with adjuvants. The immunogen can be administered by any route appropriate for antibody production, helper T cell activation, and/or cytotoxic T Lymphocyte production, such as, intravenous, intraperitoneal, intramuscular, subcutaneous, nasal, oral, and the like. The immunogen may be administered once or at periodic intervals until, for example, a significant titer of $CD4^+$ or $CD8^+$ T cell or antibodies directed against the HIV antigen is obtained. In particular, in a particularly preferred embodiment of the invention, as described above, and in our aforementioned application Ser. No. 08/695,301 (incorporated herein by reference thereto), the antigenic peptides of the invention elicit TH1 associated antibodies and other aspects of a TH1 immune response. The presence of cells may be assessed by measuring cytokine secretion in response to antigen-presenting cells pulsed with the immunogen. The antibody may be detected in the serum using conventional immunoassays.

As noted above, the administration of the vaccine or immunogen of the present invention may be for either a prophylactic or therapeutic purpose. When provided prophylactically, the immunogen is provided in advance of any evidence of HIV infection or in advance of any symptom due to AIDS, especially in high risk subjects. The prophylactic administration of the immunogen serves to prevent or attenuate AIDS in a human. When provided therapeutically, the immunogen is provided at (or after) the onset of the disease or at the onset of any symptom of the disease. The therapeutic administration of the immunogen serves to stimulate the immune response of the host.

By way of example, a vaccine prepared using recombinant expression vectors may be used. To provide a vaccine to an individual a genetic sequence which encodes for all or part of the antigenic peptide or peptide-carrier construct is inserted into an expression vector, as described above, and introduced into the mammal to be immunized. Examples of vectors that may be used in the aforementioned vaccines include, but are not limited to, defective retroviral vectors, adenoviral vectors, CMV vectors, vaccinia viral vectors, pox viral vectors, or other viral vectors (Mulligan, R. C., (1993) *Science* 260:926–932). The viral vectors carrying the nucleic sequence can be introduced into a mammal either prior to any evidence of AIDS or pre-AIDS or to mediate progression of the disease in a mammal afflicted with AIDS or pre-AIDS.

Examples of methods for administering the viral vector into the mammals include, but are not limited to, exposure of cells to the virus ex vivo, or injection of the retrovirus or a producer cell line of the virus into the affected tissue or intravenous administration of the virus. The quantity of viral vector, carrying the appropriate nucleic acid sequence encoding for the antigenic peptide or peptide-carrier construct to be administered is based on the titer of virus particles. By way of example, a range of the immunogen to be administered may be about $10^6$ to about $10^{11}$ virus particles per mammal, preferably a human. After immunization the efficacy of the vaccine can be assessed by production of antibodies or immune cells that recognize the antigen, as assessed by specific cytokine production or by disease regression. One skilled in the art would know the conventional methods to assess the aforementioned parameters. If the individual to be immunized is already afflicted with AIDS or pre-AIDS the vaccine can be administered in conjunction with other therapeutic treatments. Examples of other therapeutic treatment include, but are not limited to, protease inhibitors, reverse transcriptase, integrase, and drug combinational treatments based thereon, as currently practiced in the treatment of AIDS, or such treatments as may hereinafter be developed.

Moreover, the peptides and peptide-carrier constructs of this invention and DNA sequences encoding same may be used in a genetic immunization technique, such as disclosed in U.S. Pat. No. 5,593,972, the disclosure of which is incorporated herein in its entirety by reference thereto. According to the genetic immunization technique, the nucleotide sequence is operatively linked to regulatory sequences to enable expression in cells of an individual to which the nucleic acid molecule is administered. The resulting cells may then be used for prophylactic or therapeutic immunization. Similarly, naked DNA may be used to induce immune response, such as shown, for example, in the recently issued U.S. Pat. Nos. 5,580,859 and 5,589,466, the disclosures of which are incorporated herein in their entireties.

The invention also concerns a method for treating or preventing Acquired Immunodeficiency Complex (AIDS) by administering to a human patient in need thereof a therapeutically effective amount of the peptide-carrier construct of formula (I).

According to this invention the immune response to the Clade C peptide of SEQ ID NO:1 from the p17 protein of HIV can be directed toward at least the desired TH1 response as evidenced by the examples of the TH1 characteristic antibody IgG2a (mouse) and presumably thereby IgG3 (man). These peptides may, however, in addition to the TH1 elicited immune response, elicit a TH2 immune response, and in particular, a mixed TH1/TH2 immune response.

Accordingly, the antigenic peptides of this invention provide potentially powerful vaccines for preventing infection by, or treating cells infected by, HIV. Therefore, the present invention provides such vaccine compositions which can be used to immunize patients at risk for AIDS, or exposed to HIV, particularly HIV-1, as well as treating patients with AIDS-related Complex or with frank AIDS.

The present invention, therefore, provides antigenic p17 g protein peptides, which provide powerful vaccines for neutralizing HIV-1 and killing HIV-1 infected cells. Therefore, the vaccines of this invention can be used to immunize patients at risk for AIDS, or exposed to HIV-1 or to treat patients with AIDS-Related Complex or with frank AIDS.

When used as a vaccine in the method of this invention, the vaccine can be introduced into the host most conveniently by injection, intramuscularly, intradermally, parenterally, intranasally, orally or subcutaneously. Any of the common liquid or solid vehicles for vaccine delivery may be employed, which are acceptable to the host and which do not have any adverse side effects on the host or any detrimental effects on the vaccine. Phosphate buffered saline (PBS), at physiological pH, e.g. pH 6.8 to 7.2, preferably pH 7, may be used as a carrier, alone or with a suitable adjuvant. The concentration of immunogenic antigen may vary from about 0.5 to 200 $\mu$g/kg, such as about 25 $\mu$g/kg per injection, in a volume of clinical solvent generally from about 0.1 to 1 ml, such as about 0.2 ml, for preclinical studies in animals, and from about 0.5 ml to about 2 ml, such as about 1 ml in humans. Multiple injections may be required after the initial injections and may be given at intervals of from about 2 to 12 weeks, for example, about 2 weeks in animals and about 8 weeks in humans, when multiple injections are given. Booster immunizations may be administered or advantageous, such as from about 6 months to 2 years or even longer.

Cytotoxic T-cell responses have been observed in human volunteers immunized with CTL epitope containing peptides, however, CTL response appears to be dependent, in part, at least, upon the concentration of immunogenic antigen in the vaccine. A higher proportion of gag peptide vaccines who received a dose of from 10 to 25 μg/kg showed CTL responses than vaccines who received a higher dose of from 50 to 100 μg/kg (Sarin, et al., 1995, *Cell. Mol. Biol.* 41:401–407). These results suggest that TH-1 type cells, which have been implicated in cell mediated immunity (Clerici, et al., (1993), *Immuno. Today* 14:107–111), are induced at lower doses of CTL containing peptide vaccine. The lower proportion of CTL response among vaccines immunized with a higher dose of peptide suggest that higher vaccine doses predominantly induce TH-2 type cells involved in humoral immune response. Accordingly, the preferred concentration of immunogenic antigen in the vaccines of the present invention is in the range of from 10 to 25 μg/kg, however, a lower or a higher dose may be administered as needed.

The following are exemplary of applications for various embodiments of the antigenic peptides and constructs and compositions of this invention; but, it is understood that the invention is not restricted to the following described examples.

Embodiment 1: Use of KLH conjugate as a carrier for the invention peptide sequence to direct the immune response as a prophylactic vaccine for a TH1/TH2 directed immune response to prevent HIV infection.

Embodiment 2: Use of KLH conjugate as a carrier for the invention sequence to direct the immune response as a therapeutic vaccine for a TH1/TH2 directed immune response in HIV infected persons which may be used in conjunction with other therapies to reduce viral load and control or cure HIV infection.

Embodiment 3: Use of Human IgG, Bovine or Human serum albumin or other carrier proteins for use in the conjugate as a carrier for the invention peptide sequence to direct the immune response as a prophylactic vaccine for a TH1/TH2 directed immune response to prevent HIV infection.

Embodiment 4: Use of Human IgG, Bovine or Human serum albumin or other carrier proteins for use in the conjugate as a carrier for the invention peptide sequence to direct the immune response as a therapeutic vaccine for a TH1/TH2 directed immune response in HIV infected persons alone or in conjunction with other therapies to reduce viral load and control or cure HIV infection.

EXAMPLES

Using the same immunized mice as described above in connection with FIGS. 1, 2 and 3, the mice were bled at day 42 and the respective samples were tested in ELISA assays for cross-recognition (polyvalent response) for each of the B clade, C clade and E clade immunized mice against each of the corresponding antigenic peptides used for the immunizations, coated on the ELISA plates. Anti-sera dilutions of 1/200, 1/2000 and 1/20000 were used in the assays. The results are shown in the following Table 3. As before, the results reported in Table 3 are expressed as absorbance values at 490 nm wavelength light.

TABLE 3

| | | Clade peptide coated for ELISA evaluation | | | | | | | | |
|---|---|---|---|---|---|---|---|---|---|---|
| Immunizing Clade | | B (SEQ ID NO:4) | | | C (SEQ ID NO:5) | | | E (SEQ ID NO:6) | | |
| KLH Conjugate | Mouse # | 1/200 | 1/2000 | 1/20000 | 1/200 | 1/2000 | 1/20000 | 1/200 | 1/2000 | 1/20000 |
| B | 1038 | 0.448 | 0.137 | 0.133 | 1.027 | 0.234 | 0.153 | 0.232 | 0.192 | 0.129 |
| (SEQ ID NO:4) | 1039 | 0.995 | 0.187 | 0.157 | 0.905 | 0.187 | 0.158 | 0.753 | 0.147 | 0.142 |
| | 1040 | 0.432 | 0.194 | 0.183 | 0.760 | 0.221 | 0.180 | 0.222 | 0.177 | 0.148 |
| | 1041 | 0.223 | 0.164 | 0.167 | 0.412 | 0.175 | 0.177 | 0.229 | 0.173 | 0.131 |
| | 1042 | 0.598 | 0.172 | 0.168 | 1.014 | 0.311 | 0.188 | 0.286 | 0.161 | 0.144 |
| | 1043 | 0.428 | 0.188 | 0.166 | 0.634 | 0.221 | 0.181 | 0.239 | 0.156 | 0.133 |
| | 1044 | 0.276 | 0.174 | 0.166 | 0.402 | 0.209 | 0.181 | 0.193 | 0.162 | 0.159 |
| Group Mean | | 0.486 | 0.174 | 0.163 | 0.736 | 0.223 | 0.174 | 0.308 | 0.167 | 0.141 |
| E | 1045 | 0.337 | 0.202 | 0.191 | 1.027 | 0.234 | 0.153 | 1.786 | 1.288 | 0.470 |
| SEQ ID NO:6) | 1046 | 0.248 | 0.141 | 0.170 | 1.560 | 0.441 | 0.147 | 1.640 | 0.458 | 0.153 |
| | 1047 | 0.292 | 0.164 | 0.133 | 1.997 | 0.978 | 0.270 | 2.136 | 0.800 | 0.964 |
| | 1048 | 0.235 | 0.172 | 0.146 | 1.625 | 1.195 | 0.409 | 1.677 | 1.112 | 0.318 |
| | 1049 | 0.261 | 0.181 | 0.143 | 2.187 | 1.193 | 0.348 | 2.254 | 1.165 | 0.323 |
| | 1050 | 0.491 | 0.223 | 0.180 | 1.678 | 1.186 | 0.397 | 1.817 | 1.155 | 0.361 |
| | 1051 | 0.972 | 0.265 | 0.168 | 1.919 | 1.389 | 0.438 | 1.969 | 1.414 | 0.424 |
| Group Mean | | 0.405 | 0.193 | 0.162 | 1.713 | 0.945 | 0.309 | 1.897 | 1.056 | 0.430 |
| C | 1052 | 1.942 | 0.424 | 0.178 | 2.083 | 0.736 | 0.216 | 1.705 | 0.561 | 0.197 |
| (SEQ ID NO:5) | 1053 | 0.512 | 0.201 | 0.170 | 1.404 | 0.494 | 0.193 | 1.341 | 0.435 | 0.211 |
| | 1054 | 0.377 | 0.132 | 0.137 | 1.695 | 0.587 | 0.266 | 1.423 | 0.349 | 0.145 |
| | 1055 | 1.545 | 0.230 | 0.242 | 2.208 | 1.613 | 0.680 | 0.493 | 0.135 | 0.102 |
| | 1056 | 0.557 | 0.181 | 0.146 | 1.708 | 0.775 | 0.401 | 1.337 | 0.408 | 0.156 |
| | 1057 | 1.530 | 0.288 | 0.146 | 2.262 | 1.313 | 0.526 | 1.622 | 0.574 | 0.183 |
| Group Mean | | 1.077 | 0.243 | 0.170 | 1.893 | 0.920 | 0.380 | 1.320 | 0.410 | 0.166 |

From the results reported in Table 3 it is again observed that the antigenic peptide derived from the Clade C subtype and having an amino acid sequence beginning with amino acid in the region at position 75 to position 85 and extending for from about 30 to about 50 amino acids to amino acid in the region at position 114 to 128 is capable of inducing antibodies which exhibit strong recognition of HIV peptides from different subtypes.

What is claimed is:

1. An isolated nucleic acid molecule comprising a nucleic acid sequence encoding for a peptide having SEQ ID NO:1.

* * * * *